(12) United States Patent
Gardner et al.

(10) Patent No.: US 6,828,140 B2
(45) Date of Patent: Dec. 7, 2004

(54) ADJUSTABLE THRESHOLD SWITCH

(75) Inventors: Timothy Gardner, Jamaica Plain, MA (US); James J. Collins, Newton Center, MA (US)

(73) Assignee: Cellicon Technologies, Inc., Boston, MA (US)

(*) Notice: Subject to any disclaimer, the term of this patent is extended or adjusted under 35 U.S.C. 154(b) by 18 days.

(21) Appl. No.: 09/872,339

(22) Filed: Jun. 1, 2001

(65) Prior Publication Data

US 2003/0166879 A1 Sep. 4, 2003

Related U.S. Application Data

(63) Continuation-in-part of application No. PCT/US99/28592, filed on Dec. 1, 1999.
(60) Provisional application No. 60/110,616, filed on Dec. 2, 1998.

(51) Int. Cl.[7] ................... C12N 1/20; C12N 15/00; C12N 15/09; C12N 15/86; C07H 21/04

(52) U.S. Cl. ................ 435/252.3; 435/6; 435/69.1; 435/235.1; 435/320.1; 435/325; 435/440; 435/455; 435/471; 536/23.1; 536/24.1

(58) Field of Search ................ 435/252.3, 69.1, 435/320.1, 235.1, 440, 455, 471, 6, 325; 536/23.1, 24.1

(56) References Cited

U.S. PATENT DOCUMENTS

| | | | |
|---|---|---|---|
| 4,833,080 A | | 5/1989 | Brent et al. |
| 5,416,008 A | * | 5/1995 | Bailey et al. ............... 435/69.1 |
| 5,589,392 A | | 12/1996 | Short |
| 5,814,618 A | | 9/1998 | Bujard et al. |
| 5,972,650 A | | 10/1999 | Yao |
| 5,989,910 A | | 11/1999 | Mermod et al. |

FOREIGN PATENT DOCUMENTS

| | | |
|---|---|---|
| EP | 0 136 907 A2 | 10/1984 |
| WO | WO 99/57290 | 11/1999 |
| WO | WO 00/32748 | 6/2000 |
| WO | WO 00/65080 | 11/2000 |

OTHER PUBLICATIONS

Cormack, B.P., et al., "Facs–Optimized Mutants of the Green Fluorescent Protein (GFP)" Gene, Elsevier Biomedical Press., Amsterdam, NL, vol. 173, 1996, pp. 33–38.

Gardner, Timothy, et al: "A Theory for Controlling Cell Cycle Dynamics using a Reversibly Binding Inhibitor." Proceedings of the National Academy of Sciences of the United States, vol. 95, No. 24, Nov. 24, 1998, pp. 14190–14195.

Ishiura Masahiro, et al., "Expression of a Gene Cluster kai ABC as a Circadian Feedback Process in Cyanobacteria", Science (Washington, D.C., vol. 281, No. 5382, pp. 1519–1523.

Lutz, R., et al., "Independent and Tight Regulation of Transcriptional Units In Escherichia Coli Via the LACR/O, The TETR/O and ARAC/L1–L2 Regulatory Elements", Nucleic Acids Research, Oxford University Press, Surry, GB, vol. 6, No. 25, 1997, pp. 1203–1210.

(List continued on next page.)

Primary Examiner—Gerry Leffers
(74) Attorney, Agent, or Firm—Choate, Hall & Stewart

(57) ABSTRACT

Provided are methods and compositions for regulating gene expression in a cell. The invention provides recombinant adjustable-threshold switches which contain a first inducible promoter-regulatory gene operon and a second constitutive promoter-regulatory gene operon. A threshold amount of activating agent is required to switch the inducible promoter "on" and the constitutive promoter "off". An adjustable-threshold switch is useful to reversibly switch the expression of a gene of interest between a stable "on" state and stable "off" state in response to an activating agent at or above a threshold concentration.

15 Claims, 11 Drawing Sheets

OTHER PUBLICATIONS

Amann et al., Vectors Bearing a Hybrid trp–lac Promoter Useful for Regulated Expression of Cloned Genes in *Escherichia coli*. (1983). *Gene* 25: 167–178.

Amann et al., 'ATG Vectors' for Regulated High–Level Expression of Cloned Genes in *Escherichia coli*. (1985). *Gene* 40: 183–190.

Backman et al., Maximizing Gene Expression on a Plasmid Using Recombination in Vitro. (1978). *Cell* 13: 65–71.

Bailey et al., Molecular Genetics and Control Systems: Biochemical Engineering Fundamentals. Second Edition. Chapter 6: 307–372.

Chen et al., Molecular Design of Expression Systems: Comparison of Different Repressor Control Configurations Using Molecular Mechanism Models. (1991). *Biotechnology and Bioengineering* 38: 679–687.

Chen et al., Construction and characterization of a novel cross–regulation system for regulating cloned gene expression in *Escherichia coli*. (1993) *Gene* 130: 15–22.

Chen et al., Process Characterization of a novel cross–regulation system for cloned protein production in *Escherichia coli*. (1995). *Biotechno. Prog.* 11(4): 397–402.

Cohen, Total Control: Now you can keep bugs in line with genetic clocks and switches. (2000). *New Scientist*.

Crowl et al., Versatile expression vectors for high–level synthesis of cloned gene products in *Escherichia Coli*. (1985) *Gene* 38: 31–38.

Dedhia et al., Design of expression systems for metabolic engineering: coordinated synthesis and degradation of glycogen. (1997). *Biotechnol & Bioeng.* 55 (2): 420–426.

Gardner et al., Construction of a genetic toggle switch in *Escherichia coli*. (2000). *Nature.* 403: 339–342.

Gardner et al., Neutralizing noise in gene networks. (2000). *Nature* 405: 520–521.

Gardner, Design and Construction of Synthetic Gene Regulatory Networks. (2000). *Ph.D. Dissertation. Boston University*.

Goeddel et al., Expression in *Escherichia coli* of Chemically Synthesized Genes for Human Insulin. (1979) *Proc. Natl. Acad. Sci. USA*, 76 (1): 106–110.

Gorman et al., Regulation of the Yeast Metallothionein Gene. (1986). *Gene*, 48: 13–22.

Hadcock et al., Cross–regulation between G–protein–mediated Pathways, Stimulation of Adenylyl Cyclase Increases Expression of the Inhibitory G–protein $G_{i\alpha 2}$. (1990). *The Journal of Biological Chemistry* 265 (25): 14784–14790.

Hadcock et al., Cross–regulation between G–protein–mediated Pathways, Activation of the Inhibitory Pathway of Adenylylcyclase Increases the Expression of $\beta_2$ Adrenergic Receptors. (1991). *The Journal of Biological Chemistry* 266 (18): 11915–11922.

Hasty et al., Noise–based switches and amplifiers for gene expression. (2000). *Proc. Natl. Acad. Sci.USA.* 97(5): 2075–80.

Kaufman, High Level Production of Proteins in Mammalian Cells. (1987). *Genetic Engineering: Principles and Methods* 9: 155–198.

Kramer et al., Isolation of Yeast Genes with mRNA levels controlled by phosphate concentration. (1980). *Proc. Natl. Acad. Sci. USA*. vol. 77 (11): 6541–6545.

Lee et al., Genetically Structured Models for lac Promoter–Operator Function in the Chromosome and in Multicopy Plasmids: lac Promoter Function. (1984) *Biotechnology and Bioengineering* XXVI: 1383–1389.

Lee et al., Genetically Structured Models for lac Promoter–Operator Function in the *Escherichia coli* Chromosome and in Multicopy Plasmids: lac Operator Function. (1984). *Biotechnology and Bioengineering* XXVI: 1372–1382.

Monod et al., General Conclusions: Teleonomic Mechanisms in Cellular Metabolism, Growth, and Differentiation. (1961). *Cold Spring Harbor Symposia on Quantitative Biology* XXVI: 389–401.

Moser et al., Characterization and Complementation of pMB1 Copy Number Mutant: Effect of RNA 1 Gene Dosage on Plasmid Copy Number and Incompatibility. (1983). *Journal of Bacteriology* 154 (2): 809–818.

Oshima, Regulatory Circuits for Gene Expression: The Metabolism of Galactose and Phosphate. (1982). *The Molecular Biology of the Yeast Saccharomyces: Metabolism and Gene Expression*: 159–180.

PCT International Search Report from PCT/US99/28592.

Platt, Regulation of Gene Expression in the Tryptophan Operon of *Escherichia coli*. (1975). *The Operon.* 263–302.

Ptashne, Repressor and Its Action. (1971). *The Bacteriophage Lambda* 11: 221–237.

Seo et al., Effects of Recombinant Plasmid Content on Growth Properties and Cloned Gene Product Formation in *Escherichia coli*. (1985). *Biotechnology and Bioengineering* XXVII: 1668–1674.

Shockett et al., Diverse strategies for tetracycline–regulated inducible gene expression. (1996). *Proc. Natl. Acad. Sci. USA*. 93: 5173–5176.

Sledziewski et al., Construction of Temperature–Regulated Yeast Promoters Using the MATα2 Repression System. (1988). *Biotechnology* 6: 411–416.

Windass et al., The construction of a synthetic *Escherichia coli trp* promoter and its use in the expression of a synthetic interferon gene. (1982). *Nucleic Acids Research*. 10 (21): 6639–6657.

\* cited by examiner

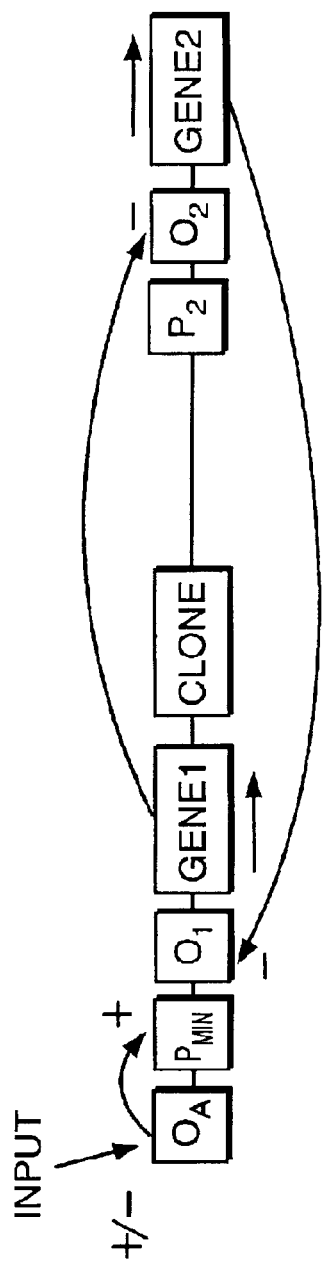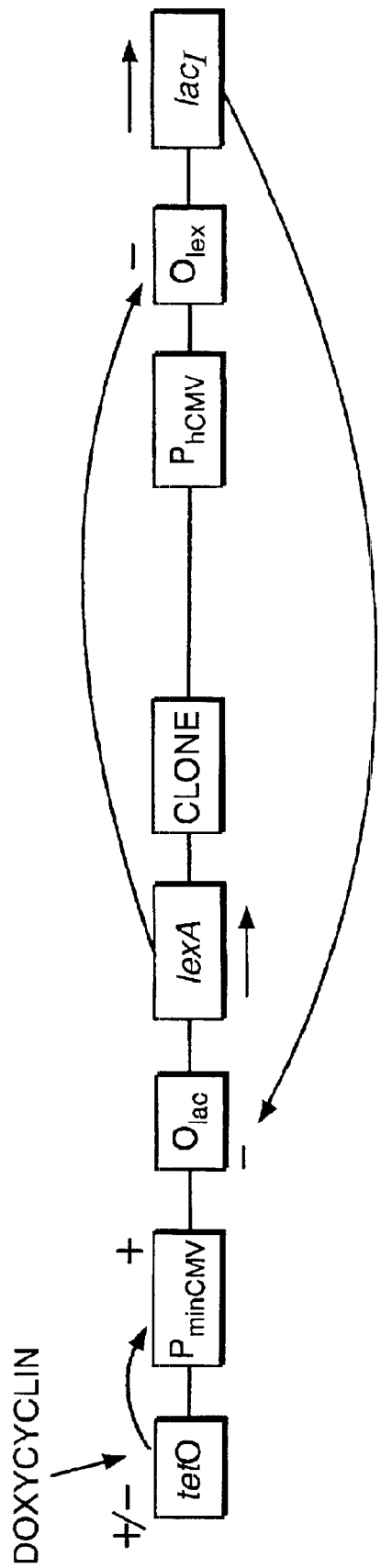
FIG. 3A
FIG. 3B

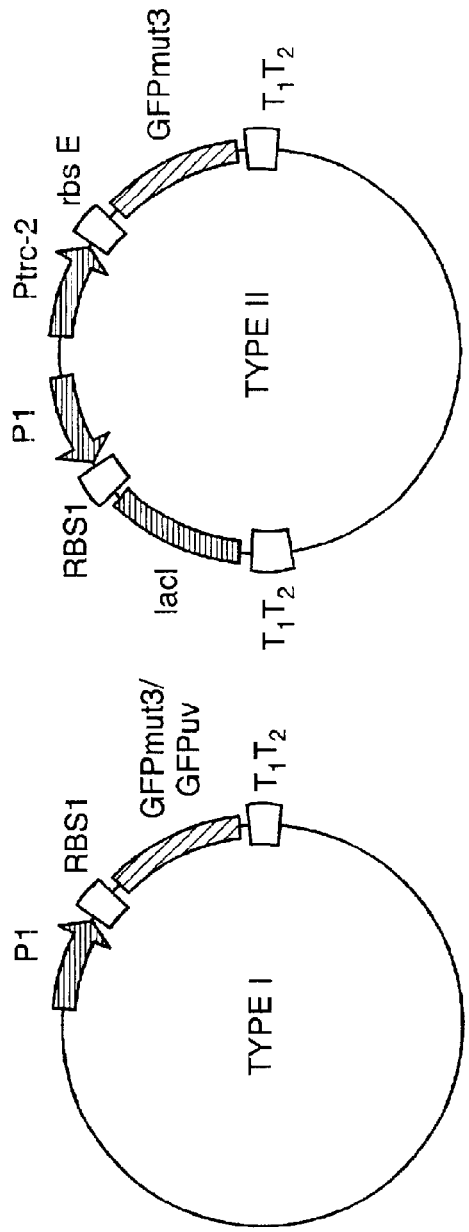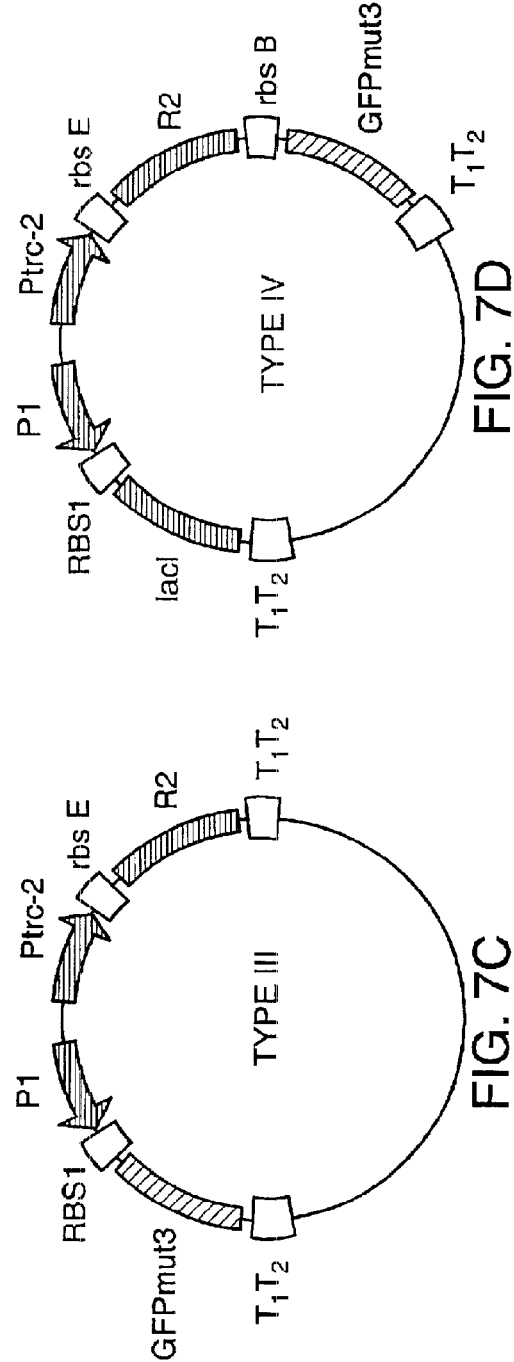
FIG. 7A  FIG. 7B  FIG. 7C  FIG. 7D

| | | |
|---|---|---|
| A | AGGAGGAAAAAAATG | (SEQ ID NO: 4) |
| B | AGGAATTTAAATG | (SEQ ID NO: 5) |
| C | AGGAAACAGACCATG | (SEQ ID NO: 6) |
| D | AGGAAACCGGTTCGATG | (SEQ ID NO: 7) |
| E | AGGAAACCGGTTATG | (SEQ ID NO: 8) |
| F | AGGACGGTTCGATG | (SEQ ID NO: 9) |
| G | AGGAAAGGCCTCGATG | (SEQ ID NO: 10) |
| H | AGGACGGCCGGATG | (SEQ ID NO: 11) |

FIG. 8B

```
gcgtcacacttcgctatgccatagcatttatccataagattagcggatcctacctgacgcttttatcgca
                                                                             l₁/l₂
cgcagtgtgaaacgatacggtatcgtaaaaataggtattctaatcgcctagaggactggactggatggaaaatagcgt
                           P_BAO actctctactgtttctctccatagatctaatgtgtggaattgtgagcggataacaatttcacacaggaaaccggt (SEQ ID NO: 12)
                                                      O_lac                                          SD
tgagagatgacaaagaggtatctagattaccacctttaacacctgtgtcctttggcca
                                From P_trc
```

FIG. 10B

ADJUSTABLE THRESHOLD SWITCH

RELATED APPLICATIONS

This application claims priority to, and the benefit of PCT/US99/28592, filed on Dec. 1, 1999, which claims priority to, and the benefit of U.S. Ser. No. 60/110,616, filed on Dec. 2, 1998, the disclosures of which are incorporated by reference herein. Related applications include: U.S. Ser. No. 09/872,868, filed Jun. 1, 2001 and U.S. Ser. No. 09/872,338, filed Jun. 1, 2001 and now U.S. Pat. No. 5,416,008, the disclosures of which are incorporated by reference herein.

FIELD OF THE INVENTION

The present invention relates to methods and compositions for regulating gene expression in a cell. In particular, the invention provides adjustable-threshold switch constructs which can selectively express or repress the expression of a gene of interest upon application of a threshold amount of an activating agent.

BACKGROUND OF THE INVENTION

Many areas of biotechnology involve regulating the expression of one or more genes of interest by applying an external agent. Typical approaches for regulating gene expression involve natural or engineered transcription factors that activate or inhibit expression of a specific gene in response to a chemical agent [Gossen and Bujard, Proc. Natl. Acad. Sci. USA, 89:5547, 1992; Rivera, et al., Nat. Med., 2:1028, 1996; Yao and Evans, Proc. Natl. Acad. Sci. USA, 93:3346, 1996; Wang, et al., Proc. Natl. Acad. Sci. USA, 91:8180, 1994]. Transcription factors often are introduced into a cell using DNA constructs that express a transcription factor and a gene of interest. Stable activation or inhibition of a transcription factor typically requires a continuous application of a chemical agent, and the level of activation or inhibition generally is proportional to the amount of agent applied, over a range of agent concentrations. However, a concentration dependant response to an activating agent often results in inconsistent expression levels in experimental, industrial, or clinical settings. The instability of many agents and their susceptibility to experimental conditions often results in variations in the amount of active agent that is added to an expression system. This can result, for example, in variations in the amount of gene activation in a system where reproducible results are desired. Therefore, there is a need in the art for methods and compositions that are useful to reproducibly obtain a chosen level gene expression.

SUMMARY OF THE INVENTION

The invention provides methods and compositions that are useful to switch gene expression between two different expression states. According to the invention, the expression of one or more genes is changed from a first expression state to a second expression state by providing a preselected amount of an agent equal to or greater than a specific concentration (threshold concentration). When the agent is removed, or its concentration drops below the threshold concentration, the switch returns back to its first expression state. An important feature of the invention is that the amount of an agent required to switch gene expression between states may be adjusted by altering the threshold concentration of the switch. The threshold concentration is determined by the properties of the genetic components used to construct the invention, as described herein. In preferred switches of the invention, one or more genes are minimally expressed, in the first expression state, while the same gene or genes are maximally expressed in the second expression state. Accordingly, an adjustable threshold switch of the invention acts to switch gene expression between "on" and "off" states.

The invention provides a recombinant adjustable-threshold switch that is characterized by two alternative expression states. In a first state, a first, inducible, promoter is substantially inactive and a second, constitutive, promoter is active. In a second state, the inducible promoter is active and the constitutive promoter is substantially inactive. Therefore, in the first state, genes that are transcribed from the constitutive promoter are expressed, and in the second state, genes that are transcribed from the inducible promoter are expressed. According to the invention, the application of the agent causes a transition from the first expression state to the second expression state if it is provided at or above the threshold concentration. If the concentration of agent drops below this level, the adjustable threshold switch returns back to the first expression state. Preferably, the transition from the first expression state to the second expression state does not occur in the absence of the agent.

With reference to FIG. 1A, the components of the recombinant adjustable threshold switch of the invention include a first nucleic acid (DNA or RNA) construct comprising a first regulatory gene ($R_1$) that is expressed from a first, inducible, promoter ($P_1$), and a second nucleic acid construct comprising a second regulatory gene ($R_2$) that is expressed from a second, constitutive, promoter ($P_2$). A product of the first regulatory gene inhibits or reduces (represses) expression of the second regulatory gene, and a product of the second regulatory gene inhibits or reduces (represses) expression of the first regulatory gene. According to preferred embodiments, either regulatory gene can be maximally expressed, but both preferably are not maximally expressed simultaneously. In a default first expression state, the constitutive promoter ($P_2$) is active, and the inducible promoter ($P_1$) is inactive (due to the absence of a sufficient amount of an activating agent and the inhibitory effect of the second regulatory gene product). The addition of an agent activates the inducible promoter ($P_1$) to switch the threshold switch of the invention to a second expression state in which the inducible promoter ($P_1$) is active and the constitutive promoter ($P_2$) is substantially inactive. However, an important feature of the invention is that an amount of the agent equal to or greater than the threshold concentration is required to cause the transition to the second expression state. In the presence of a concentration of agent (for example, activating agent) equal to or greater than the threshold concentration, expression from the inducible promoter ($P_1$) is sufficient to inhibit expression from the constitutive promoter ($P_2$). While the concentration of the agent is maintained above the threshold concentration, the second expression state is maintained. When the concentration of the activating agent falls below the threshold concentration, the first expression state is reestablished.

According to the invention, the inhibitory effects of the regulatory gene products expressed from the inducible and constitutive promoters is dependent on both the expression level of the gene product and the inherent inhibitory properties of the gene product. Expression level is a function of promoter strength, RNA stability, translational efficiency (if the gene product is a protein), and protein stability (if the gene product is a protein). Accordingly, an agent that increases the inhibitory effect of the regulatory gene product expressed by the inducible promoter can cause a switch to another expression state if the agent is provided at or above a threshold concentration. Preferably, an agent that increases the expression level of the inducible regulatory gene product by increasing transcription, translation, RNA stability, protein stability, or a combination of the above, can cause a switch in expression states if it is provided at or above a threshold concentration.

According to the invention, one or more genes of interest can be linked to either one or both of the inducible and constitutive promoters of the invention. Accordingly, expression of a gene of interest can be activated or inhibited by the presence of a threshold amount of the agent. In a preferred embodiment, a gene of interest is transcribed from either of the inducible or constitutive promoters of the threshold switch construct. Alternatively, the gene of interest can be transcribed from a separate promoter that is identical to one of the two promoters of the switch, or that is regulated in the same way as one of the promoters of the switch.

According to the invention, useful agents include natural or synthetic chemical or biological molecules, and physical conditions such as temperature, UV exposure, or osmotic pressure. Such an agent stimulates the expression or inhibitory properties of the regulatory gene product expressed from the inducible promoter as described above.

In preferred embodiments of the invention, minor variations in the amount of an agent do not cause variations in the amount of expression of a gene of interest that is regulated by an adjustable-threshold switch. The important determinant of the expression state of the gene of interest is whether the concentration of the agent is above or below the threshold concentration.

BRIEF DESCRIPTION OF THE DRAWINGS

FIGS. 3A and 3B are schematic illustrations of exemplary eukaryotic adjustable-threshold switch constructs.

FIG. 7 is a map of the four plasmid types used in the construction of a toggle switch.

In FIG. 9C, cells were initially divided, diluted and induced with IPTG for 6 hours (circles) or grown without inducer (squares).

DESCRIPTION OF THE INVENTION

The invention provides methods and compositions that extend the functionality of synthetic gene regulatory systems beyond that of currently available systems. Specifically, the invention provides adjustable-threshold gene regulatory systems that have two alternative states of gene expression. A first default state is stable in the absence of an exogenous agent. However, when the agent is applied at or above a threshold concentration, the system switches to a second state of gene expression. The second state is maintained for as long as the agent is present at or above the threshold concentration. An important feature of the invention is that the switch from one state to the other state occurs rapidly when the agent reaches the threshold concentration. According to the invention, one or more genes of interest can expressed in each state. In preferred embodiments of the invention, there are no intermediate expression levels for a gene of interest. The expression of the gene of interest is in either the "on" or "off" state depending on whether the concentration of the exogenous agent. Methods and compositions of the invention are useful for the regulating gene expression, for example in the context of gene therapy, tissue engineering, biotechnology, and biocomputing.

Figure 1A:
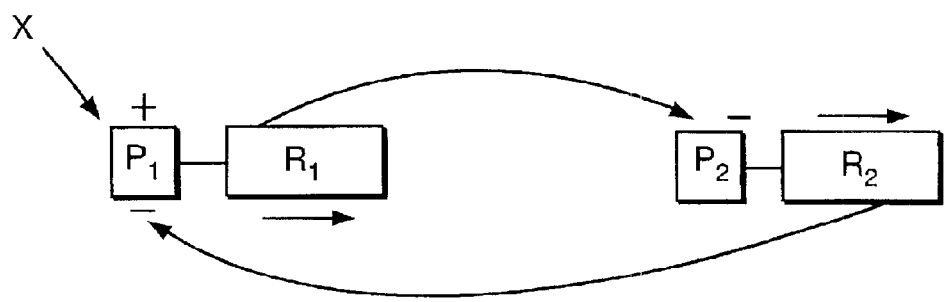
FIGS. 1A–1C are schematic illustrations of exemplary adjustable-threshold switch constructs of the invention.

FIG. 1A illustrates an exemplary adjustable-threshold switch construct according to the invention. Promoter 1 ($P_1$) is an inducible promoter. $P_1$ preferably is inactive or substantially inactive below a threshold level of an activating agent. $P_1$ is activated by one or more activating agents. Preferred activating agents include natural and synthetic chemical and biological molecules, and physical conditions such as UV light, temperature, or osmotic pressure. $P_1$ is also inhibited by a repressor protein encoded by Regulatory Gene 2 ($R_2$). Promoter 2 ($P_2$) efficiently transcribes Regulatory Gene 2 ($R_2$) unless inhibited by a repressor protein encoded by Regulatory Gene 1 ($R_1$). $P_2$ preferably is a constitutive promoter.

In the absence of the exogenous agent, the adjustable-threshold switch is in a default state in which $P_2$ actively transcribes $R_2$, and the repressor product encoded by $R_2$ represses $P_1$. Upon addition of the activating agent, expression from $P_1$ is activated. However, $P_2$ will only be inhibited if a sufficient amount of repressor encoded by $R_1$ is expressed. In order to express a sufficient amount of repressor encoded by $R_1$, a threshold amount of the exogenous agent is required. Accordingly, provided a threshold amount of the exogenous agent is maintained, the adjustable-threshold switch is in a second state in which $P_1$ is active and $P_2$ is substantially inactive. However, if the amount of the activating agent drops below the threshold amount, the adjustable-threshold switch reverts to the default state in which $P_2$ is active and $P_1$ is substantially inactive.

Figure 1B:
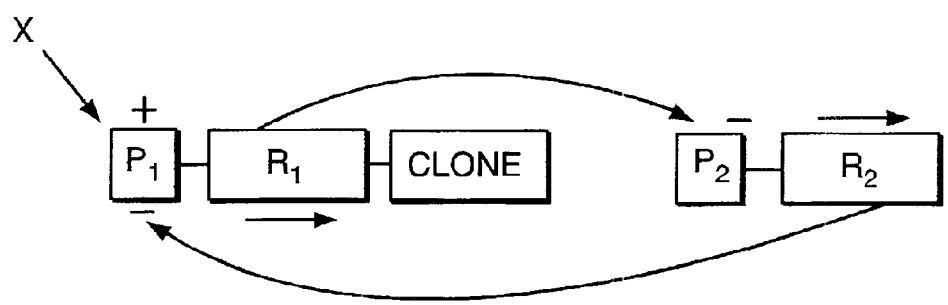
Figure 1C:
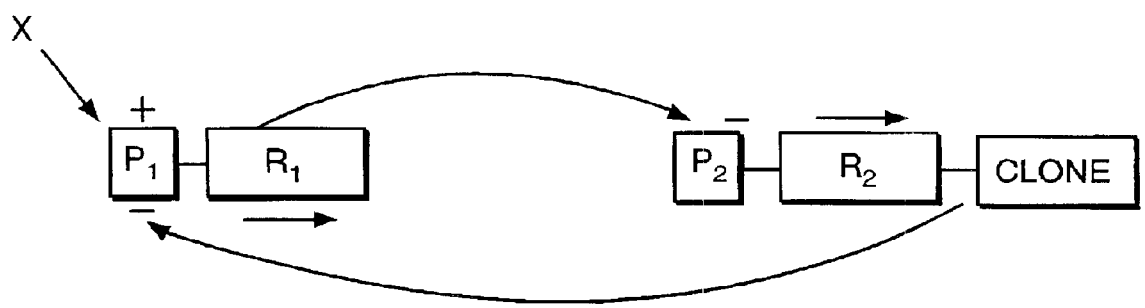

FIG. 1B shows another exemplary adjustable threshold switch in the invention. In FIG. 1B, a gene of interest (Clone) is in operable association with inducible promoter ($P_1$). When the concentration of the activating agent (Protein X) reaches a threshold concentration, expression of the gene of interest as well as $R_1$ are turned "on". Once the concentration of the activating agent once again falls below the threshold concentration, expression of the gene of interest and $R_1$ are again switched "off". FIG. 1C shows an alternative embodiment in which a gene of interest (Clone) is in operable association with constitutive promoter ($P_2$).

Accordingly, unlike a toggle switch construct (see U.S. Ser. No. 09/872,868, and PCT/US/28592) in which transcription from either romoter is equally stable, an adjustable-threshold switch construct has a "default" transcription state in which transcription of genes from the first promoter is, for example, "off" while that from the second promoter is "on". The default transcription of the gene of interest may be manipulated such that it is in a default "off" or "on" state by inserting the gene of interest downstream of either of the first or second promoter, respectively. An adjustable-threshold system of the invention is able to transition sharply from a first transcription state (e.g., suppression of $R_1$ and transcription of $R_2$) to a second transcription state (e.g., transcription of $R_1$ and suppression of $R_2$) by the application of the activating agent at a concentration that exceeds a desired threshold concentration. This sharp switching is also exemplified by the similar toggle switch constructs described in PCT/US99/28592.

According to the invention, a threshold concentration is a concentration of the activating agent that causes sufficient transcription of a first gene to induce or inhibit (repress) transcription of a second gene. Preferably, the transition from transcription of the first gene from "off" to "on" in response to the threshold concentration of the agent is sharp such that application of the agent results in a relatively high level of transcription (as compared to the level of transcription in the absence of the agent) of the first gene. According to the invention, the threshold concentration required for switching can be adjusted by modifying the inducible promoter, the constitutive promoter, the inhibitory efficacy of the regulatory gene products, or the activity of the activating agent. As described in detail herein, the strength of the promoter can be modified using methods known in the art.

1. Adjustable-Threshold Switch Components

According to the invention, the arrangement of an adjustable-threshold switch construct is similar to that of a toggle switch construct as exemplified in PCT/US99/28592 except that one of the promoters of the adjustable-threshold construct is inducible in that expression of a regulatory gene under control of the inducible promoter requires an activating agent or agents. In addition, the toggle and threshold constructs are distinguished from each other by the function of the agent that is used to bring about the transition from one transcription state to the other. Specifically, while the agent in a toggle switch construct inhibits the expression or activity of a regulatory gene product, for example, a repressor protein, the agent in a threshold switch construct activates the inducible promoter. The threshold concentration of the activating agent (e.g., activator protein X) at which the transition from one transcription state to another transcription state is achieved may be manipulated, for example, by adjusting expression of the regulatory genes as described herein.

The regulatory gene products, activating agents, and promoters used in the adjustable-threshold switch constructs of the invention are not intended to be limited to any particular type or source. Any combination of inducible promoters (and their cognate activators) and constitutive promoters (and their cognate repressors) is suitable for use in the adjustable-threshold switch construct. Suitable promoters and cognate repressors/activators are known in the art (e.g., those contained in the Swiss-Prot protein database at http://exasy.hcuge.ch/sprot/sprot-top.html) and include those listed in Tables 1 and 2, and the eukaryotic promoters $P_{hCMV}$, $P_{HSVtk}$, and $P_{SV40}$. In addition, artificial eukaryotic activators can be constructed from DNA binding proteins fused with the activation domains such as the Herpes Simplex Virus VP16 activation domain [Gossen & Bujard (1992), supra], the human B42 activation domain [Clontech Laboratories, http://www.clontech.com], or the yeast GAL4 activation domain [Darnell, et al. (1990), supra]. A cognate inducible promoter is constructed from the DNA recognition sequence of the binding domain fused with a portion of a constitutive eukaryotic promoter.

An inducible promoter (i.e., $P_1$ in FIG. 1) of an adjustable-threshold switch construct provided herein preferably directs no expression or only low levels of expression of genes under its control in the absence of a threshold concentration of an activating agent. According to the invention, a low level of expression represents a quantity of protein expressed by the gene that preferably is not detectable by, for example, an Enzyme Linked Immunosorbent Assay (ELISA). When a background level or undetectable level of the protein is measured, this may indicate that the protein is not expressed. In addition, the adjustable-threshold switch constructs require an inducible promoter that is capable of both being activated by an activating agent (e.g., X of FIG. 1A) and of being suppressed by a protein (e.g., the product of regulatory gene $R_2$ of FIG. 1A). Prokaryotic and eukaryotic promoters which satisfy these criteria are known in the art (e.g., those contained in the Swiss-Prot protein database at http://exasy.hcuge:.ch/sprot/sprottop.html), and can be constructed from combinations of inducible and repressible promoters. Examples of inducible prokaryotic promoters are listed in Table 1, and examples of repressible prokaryotic promoters are listed in Table 2.

TABLE 1

Examples of *E. coli* inducible promoters, and activators suitable for adjustable-threshold constructs

| Activator | Promoter[1] | Co-activator |
|---|---|---|
| AraC | Arabanose operon | Arabanose |
| CadC | $P_{cad}$ (CAD Operon) | Low pH |
| CRP | deoP2 | CAMP |
| CynR | Cyn operon | Cyanate |
| DsdC | Dsd operon | CRP, CAMP |
| Fh1A | Formate dehydrogenase/hydrogenase genes | Formate |
| MalT | MalPp | Maltose |
| MaoB | Monoamine oxidase gene | CRP, cAMP, tyramine |
| IlvY | IlvC gene | Acetolactate, acetohydroxybutyrate |
| UreR | Urease operon | Urea |

[1]Transcription from the promoters is induced in the presence of both activator and co-activator.

TABLE 2

Examples of *E. coli* constitutive promoters and cognate repressors, suitable for adjustable-threshold constructs

| REPRESSOR | PROMOTER |
|---|---|
| ArsR | Arsenic operon |
| AscG | ASC operon[1] |
| LacI | $P_{trc}$ |
| CscR | Sucrose operon |
| DeoR (NucR) | Deoxyribose operon |
| DgoR | DGORKAT operon |
| FruR | Fructose operon |
| GalR | Galactose operon |
| GatR | Galactitol operon |
| CI | $P_L$ |
| LexA | SOS response regulon |
| RafR | Raffinose operon |
| TetR | Tetracycline resistance operon |
| QacR | Multi-drug resistance operon |
| PtxS | Gluconate operon |

Furthermore, the adjustable-threshold switch constructs provided herein are not intended to be limited to the location of regulatory gene ($R_1$) and the gene of interest (Clone) of FIG. 1B in relation to the inducible promoter $P_1$. Rather, the adjustable-threshold switch constructs of the invention are expressly contemplated to encompass both $P_1$-$R_1$-Clone operons as well as $P_1$-Clone-$R_1$ operons so long as each of $R_1$ and Clone are operably linked to $P_1$. Moreover, the invention also contemplates having one gene of interest (e.g., Clone 1) operably linked to $P_1$-$R_1$ as well as another gene of interest (e.g., Clone 2) operably linked to $P_2$-$R_2$. In addition, the invention also contemplates having the first operon (i.e., $P_1$-$R_1$-Clone of FIG. 1B) and second operon (i.e., $P_2$-$R_2$ of FIG. 1B) encoded by a single continuous nucleic acid sequence or as two or more nucleic acid sequences.

2. Adjustable-Threshold Switch Activating Agents

According to the invention, an activating means is used to switch an adjustable-threshold switch from one expression state to another. Preferably, an activating agent increases expression from the inducible promoter in an adjustable-threshold switch construct. In general, an agent can increase expression the gene under control of the inducible promoter by increasing transcription, RNA stability, translation, protein stability, or a combination of the above. An agent of the invention can be a natural or synthetic molecule, including proteins and nucleic acids. Alternatively, an agent can be a physical property such as temperature, UV irradiation, osmotic pressure, pH, or membrane potential.

According to one embodiment of the invention, the activating agent is a molecule that increases transcription from the inducible promoter. Inducible promoters as well as their inducers are known in the art. In a preferred embodiment of the invention, the activating agent is a natural inducer of transcription. In general, an activating agent can activate transcription by binding to double stranded DNA (dsDNA) or by activating a molecule that binds to dsDNA. Useful agents include i) polynucleic acids, ii) small-molecule compounds, and iii) proteins. Preferred agents that increase transcription from an inducible promoter are listed in Table 1.

In an alternative embodiment of the invention, the expression level of a gene can be increased by increasing the translation rate of its RNA transcript. In such an activating agent may increase translation by binding to RNA or by activating a molecule that binds to RNA. Useful agents include i) polynucleic acids, ii) small-molecule compounds, and iii) proteins.

3. Adjustable-Threshold Switch Uses

The invention's adjustable-threshold switch constructs have clinical applications, such as, in gene therapy. For example, an adjustable-threshold switch construct can be constructed to activate or inactivate the expression of a desired transgene in response to a change in the concentration of a particular compound in the body. Currently, diabetics typically inject insulin into their bloodstream when their blood glucose is abnormally elevated. In a gene therapy approach, liver cells may be transfected with an insulin gene that is under the control of an adjustable-threshold switch construct. When blood glucose levels become elevated above a predetermined threshold level, the switch initiates production of insulin. This approach, therefore, may alleviate or reduce the need of the patient having to inject insulin.

The adjustable-threshold switch constructs may also be used as chemical and/or protein sensors and switches. In investigating gene expression, it may be desirable to monitor in vivo or in situ the concentration of certain chemical compounds or proteins. The adjustable-threshold switch constructs can be engineered to express a marker, for example, a fluorescent marker, for example, the Green Fluorescent Protein (Clontech) when the concentration of the protein or compound of interest rises above or falls below a particular threshold level. A highly sensitive version of this system could be used as the basis of an in vivo system for the detection of biological or chemical agents, for example, biological or chemical weapons.

Moreover, the adjustable-threshold switch constructs may also be used to activate other genes in response to changes in the cellular concentration of a particular protein or compound. For example, the switch may could be designed to activate a gene once per cell division by linking its expression to the concentration of metaphase promoting factor.

The following examples serve to illustrate certain preferred embodiments and aspects of the present invention and are not to be construed as limiting the scope thereof.

EXAMPLES

Example 1

General Considerations

The efficiency of expression of the regulatory genes in the adjustable-threshold switch constructs may be altered in prokaryotic and eukaryotic cells by manipulating one or more of the following: the strength of RNA polymerase (RNAP) binding to DNA ($K_{mu}$ or $K_{mv}$), the maximum rate of mRNA synthesis by RNAP ($\lambda_1$ or $\lambda_2$), the strength of inhibitor binding to the DNA ($K_{iu}$ or $K_{iv}$), the strength of activator binding to DNA ($K_{mx}$), the rate of translation of mRNA into functional protein ($k_1$ or $k_2$), and the rate of protein degradation, i.e., protein stability ($d_1$). These features are further described below.

i. RNAP Binding

In prokaryotic cells, recognition of the promoter sequence by RNAP is mediated by helper proteins called sigma factors that bind to two sites in the promoter: the Pribnow box (or −10 region) and the −35 region. Typically, each of these sites has an ideal sequence called a consensus sequence. The strength of binding of sigma factors, and thus the strength of RNAP binding, is determined by how closely these regions match their consensus sequence [Darnell et al (1990), supra]. Furthermore, modifications of a region upstream of the −35 region, called the UP element, have been shown to dramatically alter the rate of transcription [Estreem, ST et al. (1998) Proc. Natl. Acad. Sci. USA 95:9761–9766; Yamada, M, et al. (1991) Gene 99:109–114]. The UP element, which has also been shown to have a consensus sequence, probably enhances the binding of the RNAP complex. By modifying the sequence of the −10, −35 and UP regions, e.g., by introducing a deletion, point mutation or insertion, the strength of RNAP binding and, hence, the promoter strength, can be altered. Relative promoter strengths can be determined be quantitative assays of the expression of reporter genes such as the green fluorescent protein (GFP), β-galactosidase ((β-gal), or chloramphenicol acetyl transferase (CAT). Thus one of skill in the art may determine whether, for example, a mutation has increased or decreased the level of expression of a gene.

ii. Transcription Elongation

Once the RNAP binds to a promoter, it opens the DNA double helix and moves forward, adding ribonucleotides to the mRNA transcript. The rate of transcription is determined partially by the nucleotide content and partially by the secondary structure (if any) of the mRNA. High guanosine and cytosine content of the mRNA tends to slow the transcription rate [Darnell et al. (1990), supra]. Furthermore, secondary structures that form in the mRNA behind the transcription complex can interfere with the transcription process [Darnell et al. (1990), supra]. Although the DNA content of the coding region cannot be substantially altered (only silent mutations alter the mRNA sequence without changing the protein properties), a leader region of mRNA may be inserted upstream of the coding region. This region can be designed to slow the rate of transcription elongation. A change in the rate of transcription elongation may be determined using methods known in the art. For example, pulse labeling mRNA transcripts with radioactive nucleotides can be used to track mRNA both temporally and spatially.

iii. Inhibitor Binding

Special sequences of DNA called operators often are found within or near a promoter. The inhibitor proteins (repressors) block transcription by binding to these operators. A given repressor or activator typically recognize only one specific operator sequence. The affinity of the repressor/activator for the operator can be altered by modifying the operator sequence, e.g., by introducing a point mutation, insertion or deletion. Exemplary operator sequences useful in the practice of the invention include, for example, $O_{lac}$, $O_{lex}$, $O_{tet1}$, $O_{tet2}$, $O_{R1}$, $O_{R2}$, $O_{R3}$, $O_{L1}$, $O_{L2}$ and $O_{L3}$.

iv. Translation Rate

The rate of translation of mRNA into an amino-acid sequence is governed primarily by three factors: the ribosome binding site (RBS), the secondary structure of the mRNA, and the codon content of the coding region. The RBS typically is located 5–10 bases upstream of the start codon. Translation is most efficient when this sequence matches a consensus sequence called the Shine-Dalgarno (S D) sequence [Darnell et al. (1990), supra, Backman, K & Ptashne, M. (1978) Cell 13:65–71; Jacques, N & Dreyfus, M. (1990) Molecular Microbiology 4:1063–1067; Shine, J & Dalgarno, L. (1975) Nature 254:34–38]. Thus, translation rate can be altered by modifying the RBS, e.g., by introducing a point mutation, insertion or deletion. As in transcription, the formation of secondary structures by the mRNA can interfere with translation machinery. Thus, modification of the leader region of the mRNA or introduction of silent mutations into the coding region may be used to change translation rate. Finally, in various organisms certain codons are favored, i.e., tRNAs for certain codons are more abundant than others. Translation is more efficient when the favored codons are used [Jacques & Dreyfus (1990), supra]. Thus, a coding region can be optimized by introducing silent mutations that utilize the favored codons.

v. Protein Stability

The stability of a protein can be altered by introducing mutations into the amino acid sequence that make the protein more or less resistant to denaturation or proteolytic degradation. Powerful experimental techniques such as directed evolution, DNA shuffling and two-hybrid screening are known in the art and may be used to rapidly screen large numbers of mutant proteins for the desired stability characteristics. In addition, protein degradation rate may be altered by attaching a short, organism-specific, oligonucleotide sequence [Andersen et al. (1998) Appl. Environ. Microbiol. 64:2240–2246] to the 3' end of the gene which encodes the protein. This sequence targets the encoded protein for rapid degradation by the cell.

Design Considerations for Prokaryotic Cells

In one preferred embodiment, the cell containing the genetic cassettes of the invention is a prokaryotic cell. Preferred prokaryotic host cells, include, for example, *Escherichia coli, Bordetella pertussis, Bacillus subtillis, Salmonella typhimurium*, and *Staphylococcus aureus*. However, *E. coli* is most preferred.

While the invention is illustrated using *E. coli*, constructs containing adjustable-threshold switches which function in other prokaryotic cells are expressly contemplated to be within the scope of the invention. Switches which contain *E. coli* promoters may function without modification in related bacterial species such as gram-negative bacteria, or may be modified to bring about transcription of a gene of interest.

Figure 2:
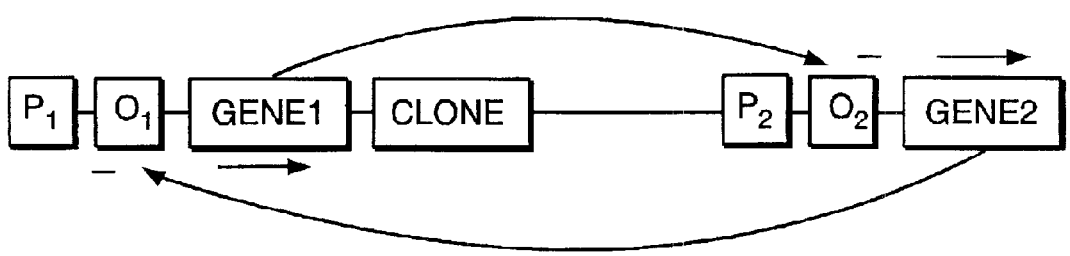
FIG. 2 is a schematic illustration of an exemplary prokaryotic or eukaryotic toggle switch construct.

FIG. 2 is a schematic illustration of a genetic toggle switch. Promoter$_1$, $P_1$, and promoter 2, $P_2$, are strong constitutive promoters from the selected host organism (prokaryotic or eukaryotic). Gene 1 encodes a repressor protein that binds to the $O_2$ operator site and represses transcription from $P_2$. Gene 2 encodes a repressor protein that binds to the $O_1$ operator site and represses transcription from $P_1$. Open arrows indicate direction of transcription. An additional gene or genes of interest (Clone) is placed under the control of $P_1$, i.e., is in operable association with $P_1$. In this configuration, $P_1$ and $P_2$ are constitutively transcribed in the selected host organism, but lack regulatory sequences needed to repress expression. These regulatory sequences are provided by the operator sites spliced within or downstream of the constitutive promoters. The operator sites, which can be derived from any *E. coli* promoter or from a promoter in the host organism, bind their associated repressor protein encoded by Gene 1 or Gene 2. Thus, two fusion promoters are created that are efficiently transcribed in the host organism and repressed by the selected *E. coli* repressors, or by a repressor chosen from the host organism. This same scheme can be applied to an adjustable-threshold switch construct to produce constructs that are functional in any selected organism. However, in the adjustable-threshold switch construct of the invention, promoter 1 is replaced with an inducible promoter.

Any repressor means may be used to construct an adjustable-threshold switch. Preferably, a repressor such as a repressor protein or nucleic acid is used, provided it reduces transcription by its cognate promoter. Similarly, any activating agent may be used to construct the adjustable-threshold switch construct so long as it increases transcription by the inducible promoter. Prokaryotic repressor-promoter-activating agent combinations which are suitable for use in the adjustable-threshold switch constructs are known in the art, such as those described in the Swiss-Prot protein database [Annotated Protein Sequence Database; http://expasy.hcuge.ch/sprot/sprottop.html].

Design Considerations for Eukaryotic Cells

It is contemplated that eukaryotic cells may be used to harbor the adjustable threshold switches of the invention. Preferred eukaryotic cells include, for example, yeast cells, plant cells, insect cells, algae and mammalian cells (including human cells). Particularly preferred eukaryotic cells include myeloma cells, fibroblast 3T3 cells, monkey kidney or COS cells, chinese hamster ovary (CHO) cells, mink-lung epithelial cells, human foreskin fibroblast cells, human glioblastoma cells, teratocarcinoma cells, HER 293 cells, L929 cells, and Hela cells.

Constitutive eukaryotic promoters typically comprise two elements: the minimal promoter sequence, for example from base pairs +1 to −65, and an enhancer sequence encompassing several hundred base pairs upstream of the minimal promoter. The minimal promoter sequence contains the TATA box consensus sequence and is necessary but not sufficient for RNA polymerase II binding and transcription. In the absence of the enhancer the minimal promoter typically does not efficiently initiate transcription (Darnell, J., et al. (1990) supra, Gossen. & Bujard, J. (1992) supra; Lubon, H., et al. (1989) Molecular and Cell Biology, 9:1342–1345; Thomsen, D R., et al. (1984) supra.] Thus, a strong eukaryotic constitutive promoter requires both a minimal promoter region and an upstream enhancer region. Exemplary strong constitutive eukaryotic promoters which direct efficient transcription in the absence of an activator and which lack an operator sequence are known in the art (e.g., those disclosed in the Swiss-Prot protein database) and exemplified by those listed in Table 3.

TABLE 3

Examples of Strong Constitutive Eukaryotic Promoters

| Promoter | Parent Organism/Gene |
|---|---|
| $P_{hCMV}$ | Human Cytomegalovirus Immediate Early Promoter [Gossen, M. & Bujard, H. (1992); Gossen, M., et al. (1995)] |
| $P_{HSVtk}$ | Herpes Simplex Virus Thymidine Kinase Promoter [Smith, GM., et al. (1988) EMBO J., 7: 3975–3982] |
| $P_{SV40}$ | Simian Virus Early Promoter [Wildeman, AG. (1988)] |
| $P_{EF-1\alpha}$ | Human [Takeuchi, Y., et al. (1999) Mar. Biotechnol., 1(5): 448–0457] |
| RSV-LTR | Rat Sarcoma Virus Promoter [Franz, WM., et al. (1997) Cardiovasc. Res., 35(3): 560–6] |
| Keratin 6 | Human [Mazzalupo, S. et al. (2001) Mech. Dev., 100: 65–69] |

While the promoters in Table 3 direct efficient transcription, these promoters typically are not repressed because they lack an operator sequence. Thus, in order to repress the exemplary promoters in Table 3, operator sequences preferably are operably linked to the promoter sequence.

In the absence of the enhancer, transcription may be efficiently induced by an activator protein that binds to a region upstream of the minimal promoter. Eukaryotic activator proteins typically consist of two functionally distinct and separable domains: the DNA binding domain (BD) which recognizes a specific sequence, and an acidic activation domain (AD) which stimulates transcription initiation. Any DNA binding protein may be fused to the AD to create an artificial activator protein [Smith, G M. (1988) supra]. As described below, this unifying feature of eukaryotic gene regulation facilitates the construction of eukaryotic versions of the adjustable-threshold switches.

To construct a eukaryotic version of the adjustable-threshold switch, constitutive eukaryotic promoters that are also repressible by a repressor protein are preferred. It has been previously shown that hybrid eukaryotic promoters (i.e., promoters composed of a constitutively transcribed eukaryotic promoter and a bacterial operator sequence) both are efficiently transcribed in the absence of the associated bacterial repressor protein, and are effectively repressed in the presence of the bacterial repressor. For example, a hybrid promoter has been constructed by splicing the E. coli LexA operator sequence into the HSV tk promoter. Expression from this promoter was reduced 10-fold in mammalian cells that synthesized the E. coli LexA repressor protein [Smith, G M. (1988) supra].

To construct a eukaryotic version of the adjustable-threshold switch, inducible eukaryotic promoters also are required. Construction of such inducible promoters is facilitated by the modular design of eukaryotic promoters. The enhancer domain from a constitutive eukaryotic promoter can be replaced with a DNA sequence recognized by the binding domain of the desired activator protein. Any E. coli DNA binding protein such as those listed in Table 1 may be used as the binding domain of an activator protein. For example, the DNA binding protein may be fused with an activator domain such as the HSV VP16 domain.

Because the fusion protein containing the binding domain and the activator domain is an artificial construct, it must be included in the adjustable-threshold construct. This can be accomplished by, for example, operably linking the gene for the fusion protein to a constitutive promoter which exists on the same vector as the adjustable-threshold switch, or on a different vector. The input to the adjustable-threshold switch is an agent, or agents, (analogous to the exemplary protein X in the prokaryotic version) which modulates the ability of the fusion protein to activate transcription.

A generic scheme for constructing a eukaryotic adjustable-threshold switch construct is illustrated in FIG. 3A. Transcription of Gene 1 from $P_{min}$ is activated by a fusion protein composed of an $O_A$-binding domain and an acidic activation domain. Activation by the activator protein may be positively or negatively modulated by a chemical signal (Input). $P_{min}$ is simultaneously inhibited at operator site, $O_1$, by the bacterial repressor protein encoded by Gene 2. Promoter 2, $P_2$, efficiently transcribes Gene 2 unless inhibited at operator site $O_2$ by the bacterial repressor protein encoded by Gene 1. Open arrows indicate direction of transcription. Clone is an additional gene or genes which may be placed under the control of $P_{min}$ or optionally under the control of $P_2$.

An exemplary construct containing the tetO operator sequence, the $P_{minhCMV}$ promoter, the $P_{hCMV}$ promoter, the lexA gene, and the lacI gene is shown in FIG. 3B. Transcription of the lexA gene from the minimal Human Cytomegalovirus Immediate Early Promoter, $P_{minCMV}$, is activated by the HSV-VP16:TetR fusion protein which binds at the tetO operator site. The HSV-VP16:TetR fusion protein is synthesized from the $P_{hCMV}$ promoter contained in a separate construct. Activation by the HSV-VP16:TetR can be positively or negatively modulated by a doxycycline, a tetracycline derived compound. $P_{minCMV}$ is simultaneously inhibited at operator site, $O_{lac}$, by the bacterial Lac repressor protein encoded by lacI. The constitutive promoter, $P_{hCMV}$, efficiently transcribes the lacI gene unless inhibited at operator site, $O_{lex}$, by the bacterial LexA repressor encoded by lexA. Open arrows indicate direction of transcription. Clone is an additional gene or genes which may be placed under the control of $P_{minCMV}$ or optionally under the control of $P_{hCMV}$. Furthermore, the HSV-VP16:TetR fusion protein may be designed such that doxycycline (a tetracycline derivative) acts as an inhibitor or, alternately, a co-activator of transcription initiation [Resnitzky et al. (1994) Mol. Cell. Biol., 14:1669; Gossen et al. (1995) Science, 268:1766]. Thus, this construct may be activated or inactivated by doxycycline.

Transfer of an Adjustable-Threshold Switch and a Gene of Interest Into a Cell

A genetic switch, and the genes of interest to which it is operably linked, may be inserted into any of several types of DNA vectors used to transfer DNA into a cell. Examples include linear DNA, plasmid DNA, shuttle vectors, modified viruses and artificial chromosomes. The vector containing the genetic switch may then be introduced into any prokaryotic or eukaryotic cell using any one of several methods including naked DNA uptake, receptor-mediated endocytosis, viral infection, lipofection, DEAE-Dextran transfection, calcium chloride transformation, calcium phosphate transfection, and electroporation. Once the vector is introduced into a cell, it may be stably maintained in the cell by applying a appropriate selective agent including, for example, neomycin, zeocin, ampicillin, and kanamycin. In other circumstances, for example, when the requisite genes are incorporated into the genome of the host cell by, for example, homologous recombination, selective agents may not be required.

Application of the Activating Agent

In order to effectively modulate expression of an adjustable-threshold switch repressor gene, an activating agent must enter the cytoplasm and possibly the nucleus of the cell containing the adjustable-threshold switch construct. Agents may be added directly to the cell's growth medium where they will pass through the cell membrane and into the cytoplasm, or they may be introduced into the bloodstream or tissues of an animal containing the switch construct. Methods suitable for introduction of an agent into an animal include intravenous injection, subcutaneous injection, transdermal uptake, and oral injection. Agents may also be added directly to cell growth medium, or introduced into an animal by the methods described above, along with additional chemical compounds that may enhance the permeability of the cell membrane to the agents [Good, L, et al. (2001) Nat. Biotech. 19:360–364]. Alternatively, the activating agent may be introduced into a cell, tissue or animal using methods typically used to mediate DNA vector uptake, including DEAE-Dextran transfection, lipofection, electroporation, and viral infection.

Example 2

Mathematical Analysis of Adjustable Threshold Switches

An important feature of an adjustable-threshold switch is the requirement of a threshold concentration of activating agent below which the inducible promoter is substantially inactive. The inducible promoter is activated (switched on) when the concentration of the activating agent is equal to or greater than the threshold concentration. In a preferred embodiment of the invention, the inducible promoter is substantially maximally activated by a threshold concentration of activating agent, and increasing the concentration of the activating agent above the threshold does not increase the activity of the promoter significantly. Accordingly, a preferred adjustable-threshold switch of the invention can adopt one of two alternative states: i) an inactive "off" state in the absence of activating agent or in the presence of sub-threshold concentrations of activating agent, or ii) an active "on" state in the presence of threshold or greater than threshold concentrations of activating agent.

Many of the features of a switch between alternative expression states of an adjustable-threshold genetic switch can be illustrated by a switch between alternative expression states of a genetic toggle switch. As discussed above, an adjustable-threshold switch preferably has a configuration of genetic elements that is similar to that of a genetic toggle switch. A key difference is that one of the promoters (the inducible promoter) of the adjustable-threshold switch is substantially inactive in the absence of activating agent. In contrast to the constitutive promoters of a genetic toggle switch, the inducible promoter of an adjustable-threshold switch is only active in the presence of a threshold or greater than threshold concentration of activating agent. Despite this important difference, the dynamics of a switch to the active state, induced by a threshold concentration of activating agent, are analogous to the dynamics of a switch from a first stable state to second stable state of a genetic toggle switch, induced by a switching agent. Similarly, when the activating agent drops below its threshold concentration, the dynamics of inactivation are similar to the dynamics of a switch between alternative expression states of a genetic toggle switch.

The following mathematical analysis illustrates predicted switching dynamics for an adjustable-threshold switch. The exemplary equations are based on a model analysis of a genetic toggle switch. The experimental examples that follow the mathematical analysis illustrate the existence of two alternative expression states for genetic toggle switch constructs. According to the invention, adjustable-threshold switches similarly exhibit two alternative expression states.

A genetic switch with an adjustable switching threshold is produced by modification of the toggle switch design described in PCT/US99/28592. The device comprises two mutually inhibitory genes (regulatory genes), one transcribed by an inducible promoter (promoter 1), and one transcribed by a constitutive promoter (promoter 2). Transcription of each regulatory gene is inhibited by the presence of the product of the other gene. Promoter 1, because it is inducible, cannot transcribe regulatory gene 1 ($R_1$ of FIG. 1B) without aid of an additional activator agent. Thus, in the absence of the activating agent (e.g. protein X of FIG. 1B), constitutive promoter 2 will dominate promoter 1 and regulatory gene 2 ($R_2$ of FIG. 1B) will be expressed. As the concentration of the activating agent (X) rises, the strength of promoter 1 rises as well. Eventually, the strength of promoter 1 exceeds that of promoter 2 and the device abruptly switches to the expression of regulatory gene 1. By manipulating the relative strengths (as described herein) of promoter 1 (when activated) and promoter 2, the concentration of the activating agent at which this transition occurs can be altered. An adjustable-threshold switch construct can be modeled using the following pair of equations (i) and (ii)

$$\frac{du}{dt} = \frac{k_1 \lambda_1 / \delta_1 x^\eta}{x^\eta + K_{mx}^\eta (1 + v^\gamma / K_{iv}^\gamma)}$$

$$\frac{dv}{dt} = \frac{k_2 \lambda_2 / \delta_2}{1 + K_{mv}(1 + u^\beta / K_{iu}^\beta)} - d_1 v$$

where, u=concentration of gene product of regulatory gene 1,
v=concentration of gene product of regulatory gene 2,
$\lambda_1$=maximum rate of synthesis of gene 1 mRNA by RNA polymerase,
$\lambda_2$=maximum rate of synthesis of gene 2 mRNA by RNA polymerase,
$\delta_1$=rate of degradation of gene 1 mRNA,
$\delta_2$=rate of degradation of gene 2 mRNA,
$k_1$=rate of synthesis of gene product of regulatory gene 1 by the ribosome,
$k_2$=rate of synthesis of gene product of regulatory gene 2 by the ribosome,
$K_{mu}$=Michaelis constant for RNAP binding and transcription of regulatory gene 1,
$K_{mv}$=Michaelis constant for RNAP binding and transcription of regulatory gene 2,
$K_{iu}$=equilibrium constant for inhibitory binding of gene product of regulatory gene 1 to promoter 2,
$K_{iv}$=equilibrium constant for inhibitory binding of gene product of regulatory gene 2 to promoter 1,
$d_1$=rate of degradation of gene products of regulatory genes 1 and 2,
$\beta$=cooperativity of binding of gene product of regulatory gene 1,
$\gamma$=cooperativity of binding of gene product of regulatory gene 2,
x=concentration of transcriptional activator of promoter 1,
$K_{mx}$=Michaelis constant for activator binding and transcription of regulatory gene 1,
$\eta$=cooperativity of binding of transcriptional activator.

The equations are based on the assumption that gene expression can be modeled using the law of mass action. Although gene expression typically does not involve a large number of particles, considerable evidence exists that such approximations provide a reasonable description of gene expression. For example, earlier work using a reconstituted enzyme system [Schellenberger et al., Adv. Enzyme Regul. 19, 257–284 (1980)] demonstrated the effectiveness of non-linear mathematics in predicting novel qualitative behaviors, including multistability and hysteresis, in biochemical reaction networks. In addition, a variety of physical and mathematical approaches, including logical or [Glass et al., J. Theor. Biol. 54, 85–107 (1975); Glass & Kauffman, J. Theor. Biol. 39, 103–129 (1973); Kauffman, J. Theor. Biol. 44, 167–190 (1974); Thomas, J. Theor. Biol. 73, 631–656 (1978); Thomas, J. Theor. Biol. 153, 123 (1991)], piece-wise linear [Tchuraev, J. Theor. Biol. 151, 71–87 (1991)], non-linear [Arkin & Ross, Biophys. J. 67, 560–578 (1994); Bhalla & Iyengar, Science 283, 381–387 (1999); Glass, J. Chem. Phys. 63, 1325–1335 (1975)], statistical-mechanical [Shea & Ackers, J. Mol. Biol. 181, 211–230 (1985); Smith et al., Math. Biosci. 36, 61–86 (1977)] and stochastic [Arkin et al., Genetics 149, 1633–1648 (1998); McAdams & Arkin, Proc. Natl. Acad. Sci. USA 94, 814–819 (1997); McAdams & Arkin, Annu. Rev. Biophys. Biomol. Struct. 27, 199–224 (1998)] formulations of the underlying biochemical dynamics, have had varying degrees of success in describing the behavior of gene networks.

The first term in each equation describes the synthesis of nascent proteins. Both transcription by the RNA polymerase and translation by the ribosome are included in the first term. Transcription, modeled with Michaelis-Menton kinetics, is competitively inhibited by the opposing gene product. Inhibition is achieved by the binding, as a homo-multimer, of one gene product to one or more sites in the opposing gene's promoter region. The multimeric interaction and the multiple binding sites are accounted for by the cooperativity exponents β and γ in the first term of each equation.

The second term describes the rate of degradation of proteins. In $E.$ $coli$, the dilution of proteins as a result of cell growth is assumed to be the major determinant of the degradation rate. Since this rate is assumed to be identical for all proteins in the cell, a single rate constant, $d_1$, is used in the model for protein degradation. However, the assumption of a single rate constant is not necessary for a functional adjustable-threshold switch. The threshold switching behavior will exist in the adjustable-threshold switch with unequal degradation rates of the proteins, but an adjustment in the promoter strengths, $\alpha_1$, and $\alpha_2$, may be necessary to maintain the threshold as described below. Additional assumptions, implicit in this model, are (i) mRNA turnover is rapid, and (ii) translation of each mRNA transcript occurs at its maximum rate, i.e. proteins are rapidly synthesized from the mRNA by an excess of ribosomes. These assumptions are supported by studies of transcription and translation [Alberts, B et al. (1994) Molecular Biology of the Cell, Garland Publishing, Inc., New York; Darnell, J et al. (1990) Molecular Cell Biology, Scientific American Books, Inc., New York].

The parameters x, $K_{mx}$, and η describe the activation of transcription by protein X. It is assumed that the activator, like the inhibitor proteins, can bind to DNA cooperatively and the activation can be modeled with Michaelis-Menton kinetics. In this model, protein X can be considered as the "input" to the switch. Increasing the concentration of protein X will cause the "output" of the switch to flip from regulatory gene 2 expression to regulatory gene 1 expression.

Figure 4:
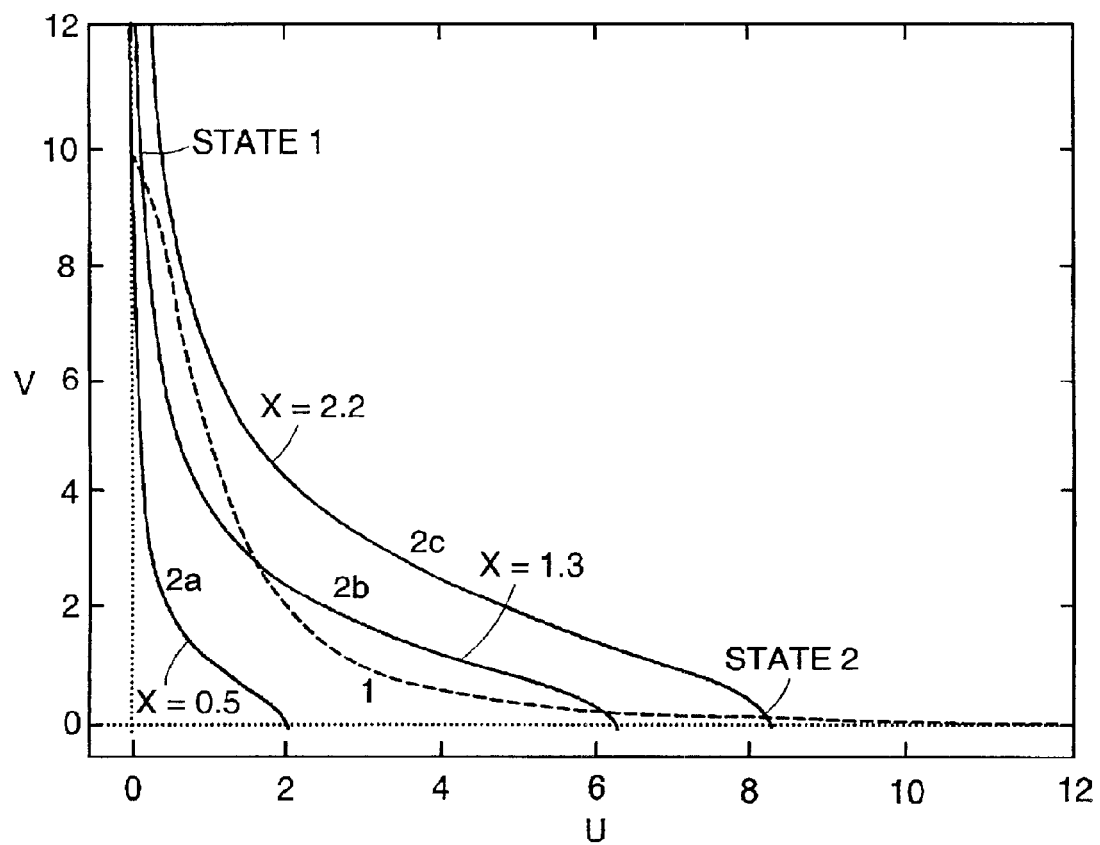
FIG. 4 is a phase plane diagram for an exemplary adjustable-threshold switch construct.

FIG. 4 provides an understanding of the switching mechanism. The dashed line is nullcline for dv/dt=0. The solid lines are nullclines for du/dt=0 for different concentrations of the transcriptional activator of promoter 1 (x). For x=0.5, state 1 is the only stable fixed point. As x increases, the system remains in state 1 until x is approximately 2. A bifurcation eliminates state 1 and the system switches dramatically to state 2.

The initial state of the system, state 1 (i.e., no activator protein, expression of regulatory gene 2, suppression of regulatory gene 1), is the stable fixed point which occurs at the intersection of nullcline 2a with nullcline 1. When the concentration of x rises, the shape of nullcline 2a is altered to nullcline 2b, causing it to intersect with nullcline 1 in two additional places. In this intermediate state, the system exhibits bi-stability analogous to that of the toggle switch construct of PCT/US99/28592. However, the system remains in state 1 in the absence of a large perturbation. As described below, this bi-stability leads to hysteresis in the switching mechanism. Depending on the intended application, hysteresis may or may not be useful. Tuning the system (e.g., by manipulating the strengths of promoter 1 ($\alpha_1$) and of promoter 2 ($\alpha_2$) as described below) allows the size of this hysteresis to be adjusted. When the concentration of x is further increased, the nullcline shifts to curve 2c, the stable fixed point at state 1 disappears and state 2 (expression of regulatory gene 1, suppression of regulatory gene 2) becomes the sole stable fixed point. Thus, the system dramatically shifts from state 1 to state 2. This shift, which was driven by the change in concentration of x, is the threshold of the system. It can be altered by adjusting the nullclines whose shape and location are determined by the parameters in equations (i) and (ii).

Analysis of this system can be simplified by rescaling time and non-dimentionalizing the variables. Equations (i) and (ii) are thus reduced to the following pair of equations (iii) and (iv):

$$\frac{d\hat{u}}{d\tau} = \frac{\alpha_1 \hat{x}^\eta}{\hat{x}^\eta + 1 + \hat{v}^\beta} - \hat{u} \quad \text{(iii)}$$

$$\frac{d\hat{v}}{d\tau} = \frac{\alpha_2}{1 + \hat{u}^\gamma} - \hat{v} \quad \text{where,} \quad \text{(iv)}$$

$\tau = d_1 t,$ $\hat{u} = \dfrac{u}{K_{iu}(1/K_{mv}+1)^{1/\beta}},$ $\hat{v} = \dfrac{v}{K_{iv}},$ $\hat{x} = \dfrac{x}{K_{mx}},$ $\alpha_1 = \dfrac{k_1 \lambda_1/\delta}{d_1 K_{iu}(1/K_{mv}+1)^{1;\beta}}$ and $\alpha_2 = \dfrac{k_2 \lambda_2/\delta_2}{d_1 K_{iv}(1+K_{mv})}$ Nine parameters in the original equations have been collapsed into two dimensionless parameters $\alpha_1$ and $\alpha_2$. These parameters describe the efficiency (i.e. the maximum strength) of gene expression achieved by the constitutive and inducible promoters. Since they incorporate multiple parameters, including the rate of transcription, translation and degradation of the regulatory proteins in the adjustable-threshold switch, $\alpha_1$ and $\alpha_2$ may be considered the "effective promoter strength" of the constitutive and inducible promoters. By condensing nine parameters into just two parameters describing the effective promoter strength, the analysis of the effects of only five parameters (i.e., x, $\alpha_1$, $\alpha_2$, η, and γ)

is required. As used herein, promoter strength will be considered synonymous with "effective promoter strength."

Figure 5A:
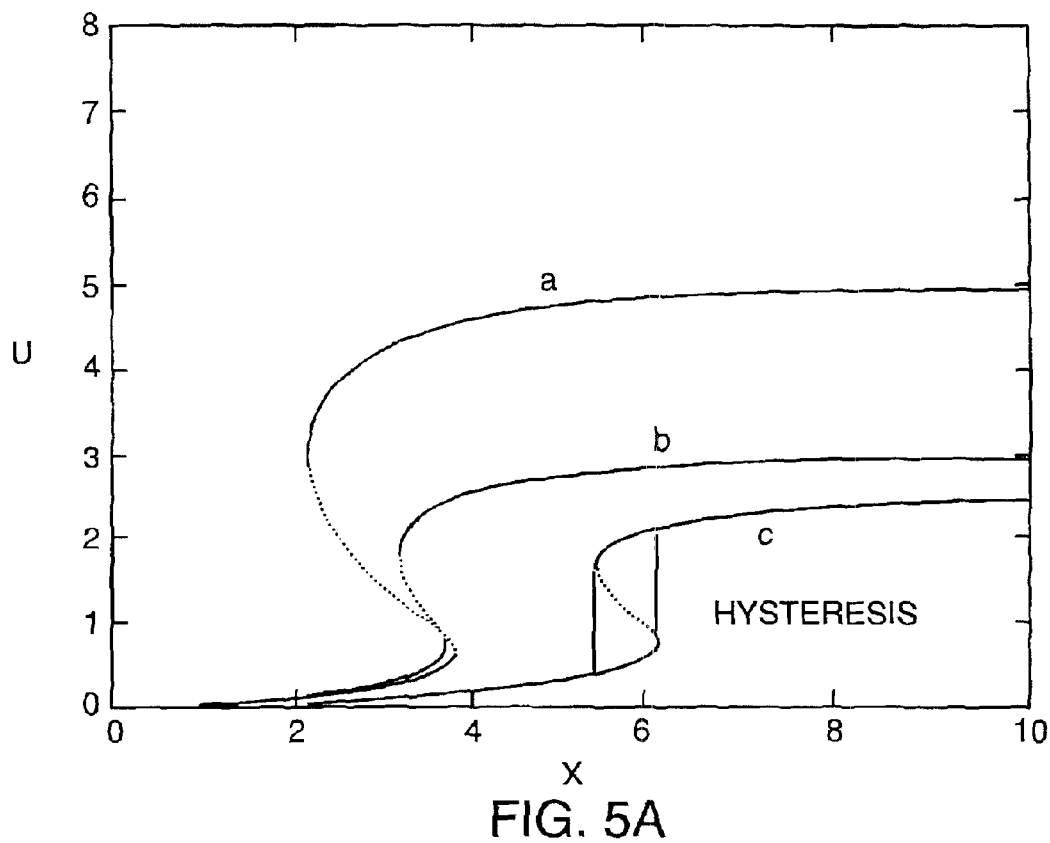
FIGS. 5A and 5B are graphs showing the structure of the threshold in exemplary adjustable threshold switches of the invention.
Figure 5B:
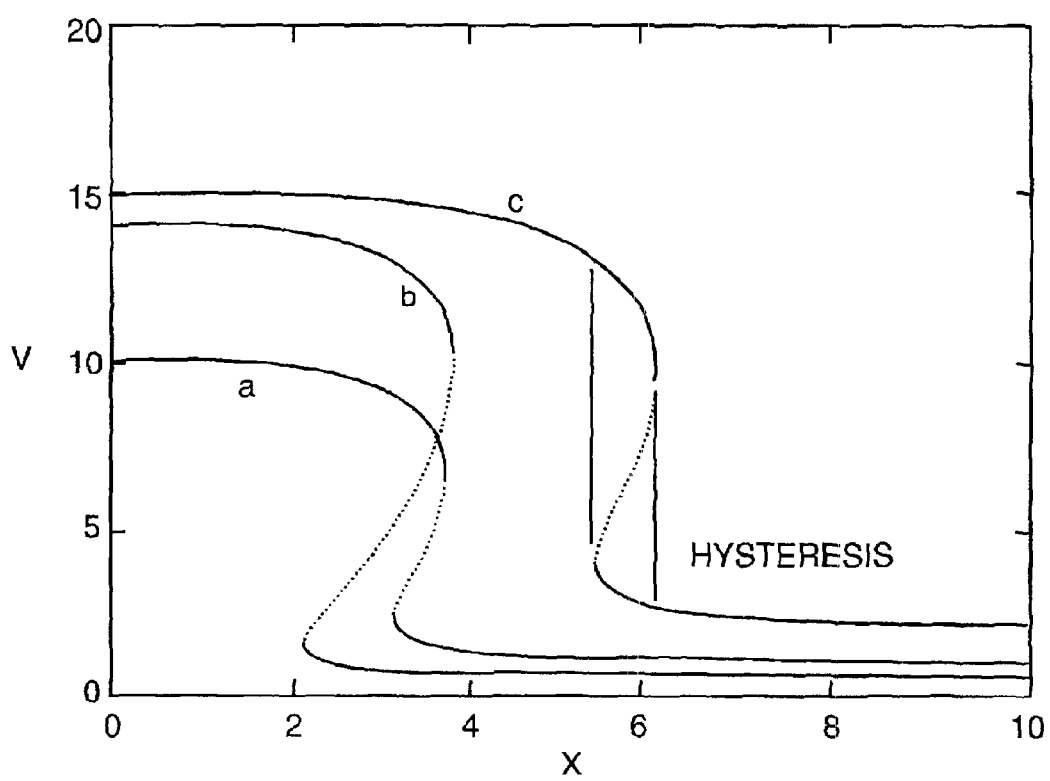

FIG. 5 shows the structure of the threshold. FIG. 5A shows the concentration of regulatory gene product 1 (u) as a function of activator (x) concentration. FIG. 5B shows the concentration of regulatory gene product 2 (v) as a function of activator (x) concentration. Hysteresis exists at the switching threshold as indicated by the arrows in FIGS. 5A and 5B. Both the location of the threshold and size of the hysteresis can be manipulated independently. Parameter values: $\alpha_1=5$, $\alpha_2=14$ (curve a in FIGS. 5A and 5B), $\alpha_1=3$, $\alpha_2=10$ (curve b in FIGS. 5A and 5B), $\alpha_1=2.7$, $\alpha_2=15$ (curve c in FIGS. 5A and 5B), $\eta=\gamma=2$ (all curves in FIGS. 5A and 5B). FIG. 5 shows the steady state concentrations of proteins u and v versus the concentration of x for several values of parameters $\alpha_1$, and $\alpha_2$. This figure reveals more clearly the nature of the threshold and the associated hysteresis. It also demonstrates that both the location of the threshold and the size of the hysteresis can be tuned.

Figure 6A:
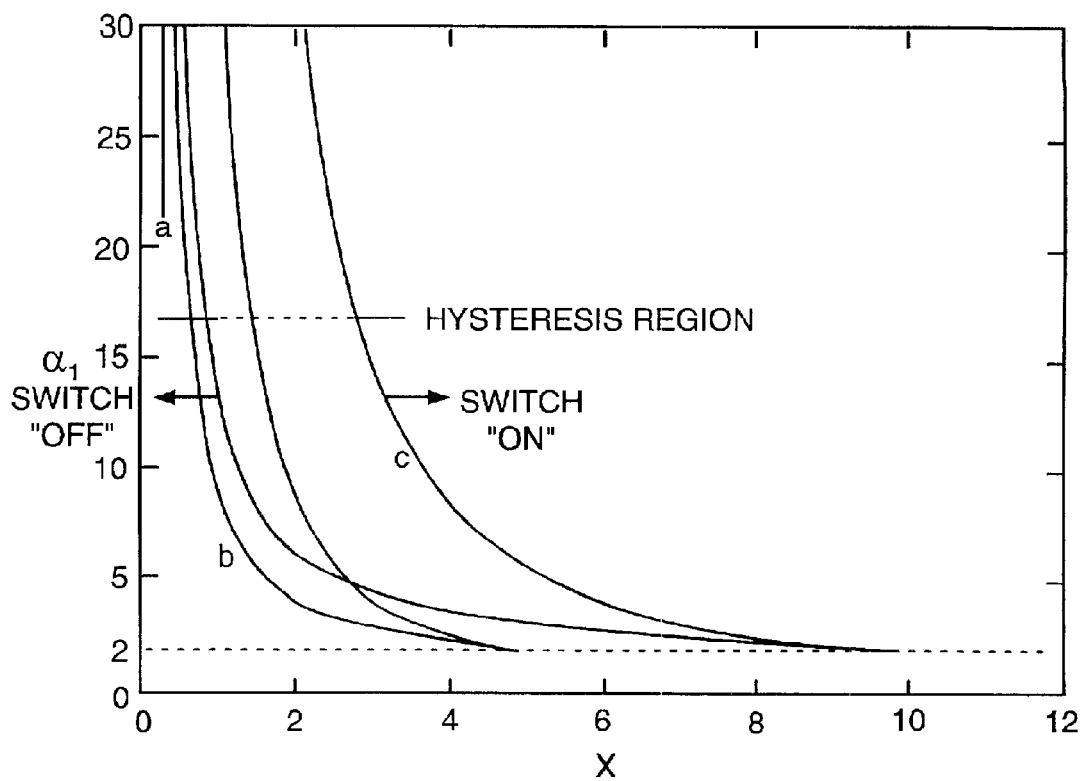
FIGS. 6A and 6B are graphs showing the size of the hysteresis and the locations of the threshold for a range of promoter strengths for α1 (FIG. 6A) and α2 (FIG. 6B) in an exemplary adjustable-threshold switch of the invention.
Figure 6B:
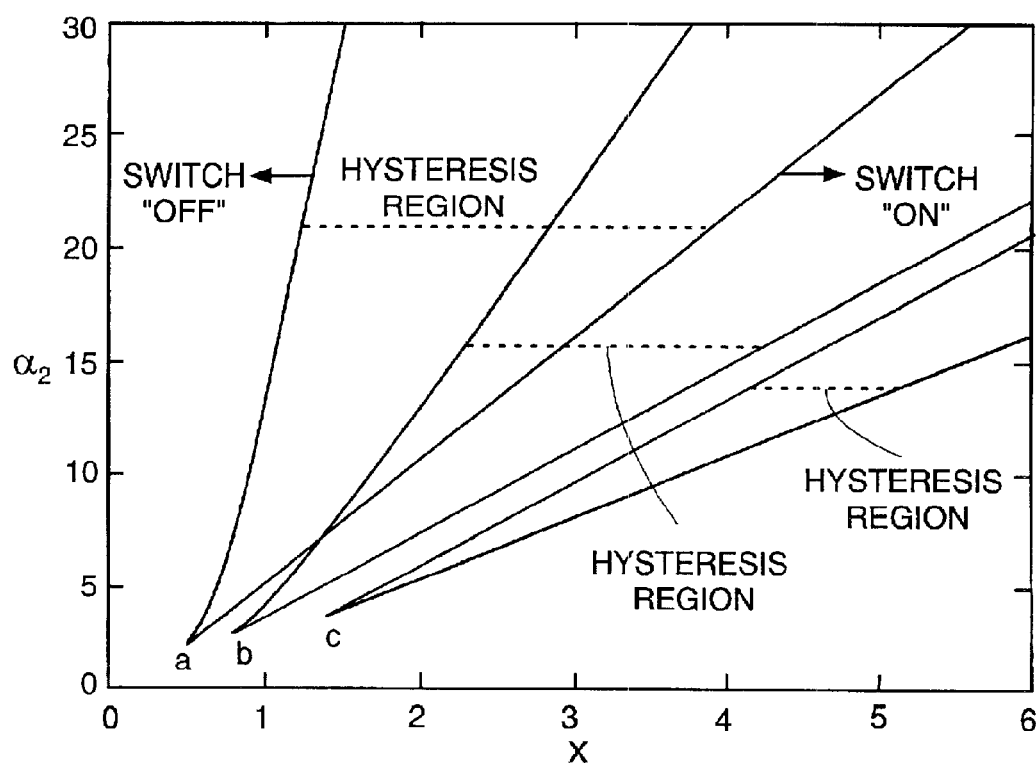
Figure 8A:
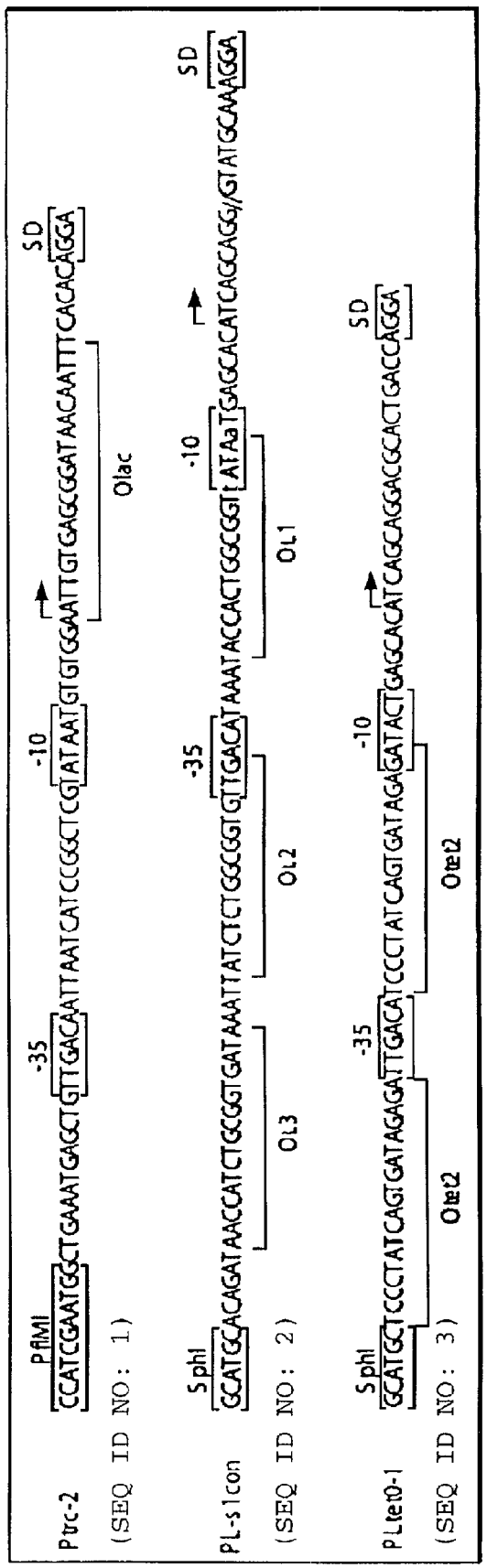
FIG. 8 shows the nucleic acid sequence of promoters (8A) and ribosome binding sites (8B) used to construct toggle switch plasmids.

The effects of parameters $\alpha_1$ and $\alpha_2$ on the threshold and hysteresis are more fully illustrated in FIG. 6. FIG. 6A shows $\alpha_1$ as a function of activator (x) concentration and FIG. 6B shows $\alpha_2$ as a function of activator (x) concentration. FIG. 6 is a bifurcation diagram showing the size of the hysteresis and the location of the threshold for a range of values of promoter strengths in an adjustable-threshold switch construct. In FIGS. 6A and 6B, the lines demarcating the hysteresis region represent saddle-node bifurcations. To achieve minimal hysteresis, a weak promoter 1 is desirable; however, a minimal promoter strength exists beyond which no threshold will be generated. This minimal strength can be determined through experimental adjustment and testing of promoter strengths as described above in Example 1. Increasing the strength of promoter 2, or decreasing the strength of promoter 1, translates the threshold to higher values of x. Parameter values: $\eta=\gamma=2$ for all curves; (6A) $\alpha_2=2$ (curve a), $\alpha_2=10$ (curve b), $\alpha_2=20$ (curve c); (6B) $\alpha_1=10$ (curve a), $\alpha_1=5$ (curve b), $\alpha_1=3$ (curve c). Increases in $\alpha_2$ (i.e., the strength of promoter 2) move the switching threshold to larger concentrations of activating agent x, but also increase the size of the hysteresis. Reductions in $\alpha_1$, the maximum strength of promoter 1, also move the threshold to higher concentrations of activating agent x and simultaneously reduce the size of the hysteresis. Thus, a switch with the desired threshold and hysteresis characteristics can be designed by choosing promoters of appropriate strengths (i.e., those strengths which produce the desired threshold and hysteresis characteristics. Strengths may be experimentally adjusted according to the qualitative predictions of the theory. Manipulations and assays are the same as those described for the toggle switch construct). Finally, FIG. 8A shows that there are absolute limits to the adjustability of the threshold. For very low values of $\alpha_1$, no switching occurs regardless of the strength of promoter 2. Furthermore, in the experimental system, the promoter strength will have a physically determined maximum that will place an upper limit on the location of the switching threshold.

The above discussion shows that, in one embodiment, a sharp rise in transcription of a gene of interest preferably occurs (a) where the first and second repressor proteins form homo-dimers, both $\alpha_1$ and $\alpha_2$ have a value of greater than 2, and (b) where the first and second repressor proteins form homo-multimers other than dimers, either $\alpha_1$, or $\alpha_2$ have a value greater than 1. The minimum permissible value of $\alpha_1$ or of $\alpha_2$ approaches 1 as the degree of multimerization increases, but it doesn't fall below 1.

Example 3

Construction of an Exemplary Toggle Switch

This Example demonstrates the successful construction and testing of a variety of toggle switches which exhibit bi-stability and an ideal switching threshold.

All the toggle switches described herein were constructed using *E. coli* plasmids conferring ampicillin resistance and containing the pBR322 ColEl replication origin. Each toggle switch comprised two repressors and two constitutive promoters wherein each promoter was inhibited by the repressor transcribed by the opposing promoter. The toggle switch genes were arranged as a Type IV plasmid as shown in FIG. 7D. In FIG. 7D, the promoters are denoted by solid rectangles with arrowheads, genes are denoted with solid rectangles, ribosome binding sites and terminators ($T_1, T_2$) are denoted by outlined boxes. The Ptrc-2 promoter ($P_2$) with RBS-E (RBS2) and the lacI gene ($R_1$) were used in all Type II, III and IV plasmids (FIGS. 7B, 7C and 7D, respectively). RBS-B (shown in FIG. 8) was used for the reporter gene in all Type IV plasmids. Different $P_1$ promoters, RBS1 ribosome binding sites, and/or $R_2$ repressors, were used for the various toggle switches. The two opposing promoters and repressor genes were arranged back-to-back in opposite orientation to minimize unintended phenomena such as transcription read-through and antisense transcription. Though all genes were contained on a single plasmid, the two halves of the toggle can, in principle, be placed on separate plasmids without altering the functionality of the toggle.

i. Plasmid Construction

Two classes of toggle switches were constructed—the pTAK class (Class 1) and the pIKE class (Class 2). Both classes contained the Lac repressor (lacI) in conjunction with the Ptrc-2 promoter for the first promoter-repressor pair. For the second promoter-repressor pair, the pTAK plasmids (Class 1) contained the $P_L$slcon promoter in conjunction with a temperature-sensitive mutant of the λ repressor (cIts). The pTAK plasmids were switched between states by a pulse of IPTG or by a thermal pulse. For the second promoter-repressor pair, the pIKE plasmids (Class 2) contained the $P_L$tetO-1 constitutive promoter in conjunction with the TetR repressor (tet R). The pIKE plasmids were switched between states by a pulse of IPTG or a pulse of anhydrotetracycline (aTc). In total, four variants of the pTAK based toggles and two variants of the pIKE based toggles were constructed and tested herein.

Plasmids were constructed using basic molecular cloning techniques described in standard cloning manuals [Ausubel et al. in *Current Protocols in Molecular Biology* (Wiley, New York, 1987); Sambrook et al. in *Molecular Cloning: A Laboratory Manual* (Cold Spring Harbor Laboratory Press, Plainview, N.Y., 1989)]. Restriction enzymes were purchased from New England Biolabs and Promega; PfuTurbo polymerase was purchased from Stratagene; all other enzymes were purchased from New England Biolabs; all synthetic oligonucleotides were purchased from Operon Technologies. All genes, promoters and transcription terminators were obtained by PCR amplification using PfuTurbo proofreading polymerase and synthetic primers with overhanging ends containing the appropriate restriction sites. Ribosome binding sites were included in the overhanging ends of the primers. Site mutations were performed using either the Stratagene QuickChange or ExSite protocols in accordance with the manufacturers instructions.

Genes, promoters and transcription terminators were obtained as follows: Ptrc-2 from pTrc99a (AP Biotech), $P_L$ from pXC46 (ATCC), $P_L$tetO-1 by total synthesis according to the published sequence [Lutz & Bujard (1997) Nucleic Acids Res. 25:1203–1210], lacI from pTrc99a, cIts from pGW7 (ATCC), tetR from pcDNA6/TR (Invitrogen), gfpuv from pGFPuv (Clontech), gfpmut3 from pJBAI 11 (gift of J. B. Andersen, Technical University of Denmark), and rrnT1T2 terminators from pTrc99a. All plasmids contained the ampicillin resistance region and ColEl origin of replication from the pTrc99a plasmid. All cloning was performed by TSS transformation [Ausubel et al. in *Current Protocols in Molecular Biology* (Wiley, New York, 1987)] into either *E. coli* strain JM2.300 (CGSC), JC158 (CGSC), or TAP106 (ATCC). DNA sequencing was performed using a Perkin-Elmer ABI Prism 377 Sequencer.

In all toggle plasmids, the gfpmut3 reporter gene was arranged as the second cistron downstream of the Ptrc-2 promoter. Thus, transcription from Ptrc-2 (and repression of $P_1$) results in the expression of GFPmut3. For clarity, this state is termed the "high" state. The opposing state, in which $P_1$ is transcribed and Ptrc-2 is repressed, is termed the "low" state. Unless otherwise indicated, GFPmut3 is the reporter used in all plasmids. Gfpmut3, a mutant of wild-type GFP containing S65G and S72A substitutions, is optimized for flow cytometry [Cormack et al. (1996) Gene 173:33–38]. This mutant is approximately 50–70 times brighter than GFPuv when expressed in *E. coli* and assayed in a FACS-Calibur flow cytometer.

The promoters used in the toggle were $P_L$tetO-1 (TetR repressed), Ptrc-2 (LacI repressed) and $P_L$slcon (CI repressed). The ranked order of the transcriptional efficiencies of the promoters is $P_L$slcon>Ptrc-2>$P_L$tetO-1. In all variants of the toggle switch, the sequence of the three promoters was unchanged. The rates of synthesis of the repressors ($\alpha_1$ and $\alpha_2$ in the model) or the reporter genes are modified by exchanging the downstream ribosome binding sites (RBS). The structures of the three promoters and the various ribosome binding sites used in the toggle switches are illustrated in FIGS. 8A and 8B, respectively (SEQ ID NOs: 1–11). In FIG. 8A, the upstream limit of each promoter is marked by the indicated restriction site. Operator sites are marked by a single underbracket. The initiation of transcription is denoted with arrows. SD denotes the Shine-Dalgarno sequence. Mutations in the -10 sequence of $P_L$slcon are indicated with lowercase letters. In FIG. 8B, the Shine-Dalgarno sequences "AGGA" and start codons "ATG" are presented. The various sequences are ranked in order of their translational efficiency (A being the highest, H being the lowest)

Bases -48 to +27 of the Ptrc promoter, where +1 is the initiation of transcription, were amplified by PCR from pTrc99a to form the Ptrc-2 promoter. Ptrc-2 is a highly efficient fusion of the Ptrp and Plac promoters and is nearly identical to the commonly used Ptac promoter. $P_L$slcon is a shortened version of the wild-type $P_L$ promoter with additional mutations conferring a consensus -10 sequence. $P_L$slcon was amplified from bases -75 to the Shine-Dalgarno sequence of pXC46. Thus $P_L$slcon eliminates the $P_{L2}$ secondary promoter and the L1 and L2 integration host factor binding sites of the wild-type $P_L$ promoter [Giladi et al. (1992) J. Mol. Biol. 224:937–948]. Elimination of $P_{L2}$, LI, L2 and introduction of the -10 mutations serve to weaken the native strength of the extremely strong $P_L$ promoter while retaining all three operators for λ repressor binding. The $P_L$tetO-1 promoter, obtained through total synthesis according to the published sequence [Lutz & Bujard (1997) Nucleic Acids Res. 25:1203–1210], contains two copies of the O2 operator of the TnIO tetracycline resistance operon—one between the consensus -35 sequence and the -10 sequence of $P_L$, and one upstream of the -35 sequence. The $P_L$tetO-1 promoter was substantially less efficient than both Ptrc-2 and $P_L$slcon, but it was effectively repressed by the wild-type TetR repressor.

ii. Strains, Growth Conditions, Chemicals

The host cell for all promoter assays and toggle switch experiments was *E. coli* strain JM2.300 [λ-, lacI22, rpsL135 (StrR), thi-1] (CGSC strain 5002). JM2.300, which contains few mutations and is a fast growing strain that can tolerate enormous overexpression of plasmid-bound genes. Because JM2.300 contains no λ repressor and carries a non-functional Lac repressor (lacI22), it is considered to be a suitable host for the toggle switch.

All cells were grown in LB medium (Difco) with 100 μg/ml ampicillin plus inducers as indicated in the text. All Type I and pIKE series plasmids were grown at 37±1° C., unless otherwise indicated. All pTAK series plasmids were grown at 32±1° C. except during thermal induction. Thermal induction was carried out at 42±1° C., unless otherwise indicated. For all expression tests, cells were maintained in logarithmic growth phase by periodic 500–1000-fold dilution into fresh medium.

Ampicillin and IPTG were purchased from Sigma. Anhydrotetracycline was purchased from ACROS Organics. All other chemicals were obtained from Fisher.

iii. Assay of Gene Expression and Promoter Strength

The following expression data was collected using a Becton-Dickinson FACSCalibur flow cytometer with a 488 nm argon excitation laser and a 515–545 nm emission filter. Prior to each assay, cells were pelleted and resuspended in 0.22 μm filtered phosphate buffered saline (58 mM $Na_2HPO_4$, 17 mM $NaH_2PO_4$, 68 mM NaCl, pH=7.4). Cells were assayed at low flow rate and fluorescence was calibrated using InSpeck Green fluorescent beads (Molecular Probes). All measurements of gene expression were obtained from three independent cultures maintained simultaneously under identical conditions. For each culture, 40,000 events were collected. All flow data were converted to ASCII format using MFI (E. Martz, University of Massachusetts, Amherst, available at http://marlin.bio.umass.edu/mcbfacs/flowcat.html\##mfi) and analyzed with Matlab (Mathworks).

The strengths, in calibrated fluorescence units, of the promoter/RBS pairs used to construct the toggle switches are listed in Table 4. Measurements of promoter strengths were performed using Type I plasmids (FIG. 7A) and assays were performed as described above. Leakage expression from the promoters under fully repressed conditions is also listed in Table 4.

TABLE 4

Gene Expression by Plasmids

| PLASMID | TYPE | P1 | RBS1 | RBS2 | GFP EXPRESSION |
|---|---|---|---|---|---|
| Bare Promoters | | | | | |
| pMKN7a* | I | Ptrc-2 | E | — | 732 ± 108 |
| pBAG102 | I | $P_L$tetO-1 | C | — | 5.5 ± 0.1 |
| pBAG103 | I | $P_L$tetO-1 | A | — | 660 ± 42 |
| pBRT21.1* | I | $P_L$slcon | D | — | 9,390 ± 840 |
| pBRT21.1*† | I | $P_L$slcon | D | — | 14,300 ± 400 |
| pBRT123 | I | $P_L$slcon | G | — | 387 ± 21 |
| pBRT124 | I | $P_L$slcon | F | — | 972 ± 43 |
| pBRT125 | I | $P_L$slcon | H | — | 15.9 ± 3.2 |
| LacI Repression | | | | | |
| pTAK102 | II | $P_L$slcon | D | — | 36.0 ± 3.8 |
| pTAK103a | II | $P_L$slcon | G | — | 137 ± 8 |
| cI Repression | | | | | |
| pTAK106 | III | $P_L$slcon | D | — | 2.5 ± 0.3 |
| pTAK107 | III | $P_L$slcon | G | — | 2.0 ± 0.1 |

TABLE 4-continued

Gene Expression by Plasmids

| PLASMID | TYPE | P1 | RBS1 | RBS2 | GFP EXPRESSION |
|---|---|---|---|---|---|
| TetR Repression | | | | | |
| pIKE108 | III | $P_L$tetO-1 | A | — | 5.8 ± 1.0 |
| pIKE110 | III | $P_L$tetO-1 | C | — | 2.3 ± 0.2 |
| Toggles | | | | | |
| pTAK117 | IV | $P_L$slcon | D | B | Bistable |
| pTAK130 | IV | $P_L$slcon | G | B | Bistable |
| pTAK131 | IV | $P_L$slcon | F | B | Bistable |
| pTAK132 | IV | $P_L$slcon | H | B | Bistable |
| pIKE105 | IV | $P_L$tetO-1 | A | B | Monostable |
| pIKE107 | IV | $P_L$tetO-1 | C | B | Bistable |

*Estimated from flow-cytometer assay of GFPuv-expressing promoters.
†Grown at 32° C.

The efficacy of repression was tested using Type II plasmids (for LacI repression) (FIG. 7B) or Type III plasmids (for cI or TetR repression) (FIG. 7C). The efficiency of the three repressors, as used in the toggle switches can be estimated by comparing the strength of the bare promoters in Type I plasmids against their leakage expression under repressed conditions. For example, the extremely efficient λ repressor (cI), expressed from Ptrc-2-E, achieves ~6000 fold (14,300/2.5) repression of the $P_L$slcon-D promoter (Table 4). On the other hand, the TetR repressor, also expressed from Ptrc-2-E, achieves only ~100 fold (660/5.8) repression of the $P_L$tetO-1-A promoter (Table 4).

iv. Demonstration of Bi-Stability

In order to test the limits of bistability of the toggle switch, the a1 parameter was varied experimentally by inserting RBS 1 sequences of varying efficiency into Class 1 and Class 2 toggle switches of Type IV. Four pTAK series plasmids (Class 1) were constructed with RBS 1 sequences D,F,G and H, and two pIKE series plasmids (Class 2) were constructed with RBS1 sequences A and C (Table 4). All four pTAK plasmids exhibited bistability, while only one pIKE plasmid (PIKE107) exhibited bistability.

Figure 9A:
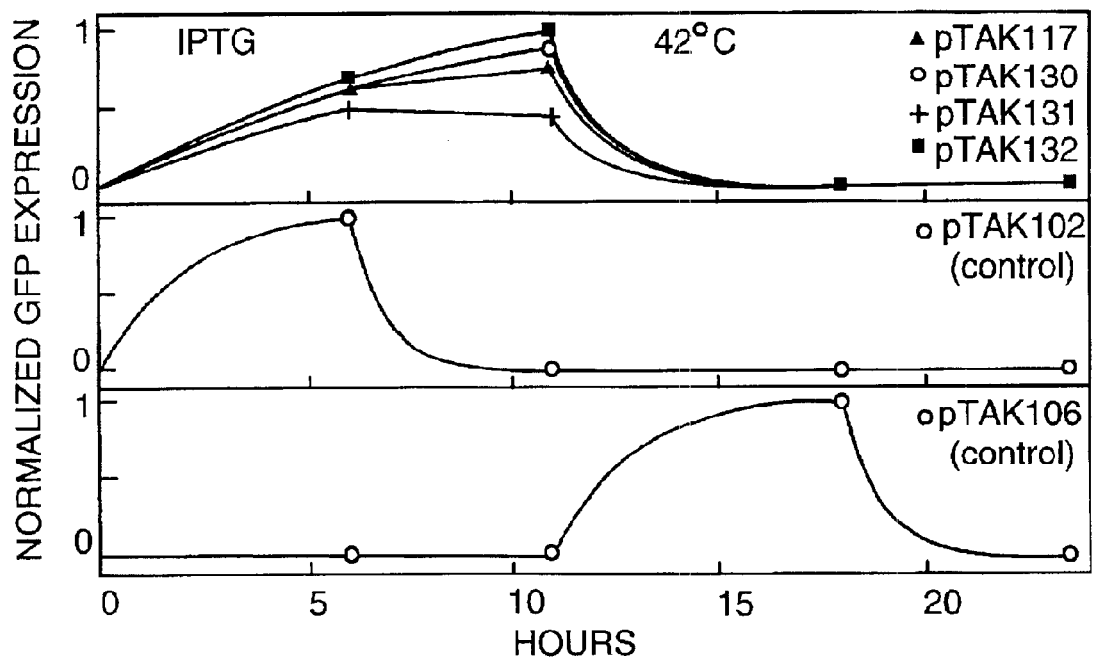
FIGS. 9A–9C are graphs demonstrating bistability of exemplary toggle switches: Class 1 toggle switches (pTAK) and controls (FIG. 9A); Class 2 toggle switches (pIKE) and controls (FIG. 9B); and long-term test of pTAKI17 bistability (FIG. 9C).
Figure 9B:
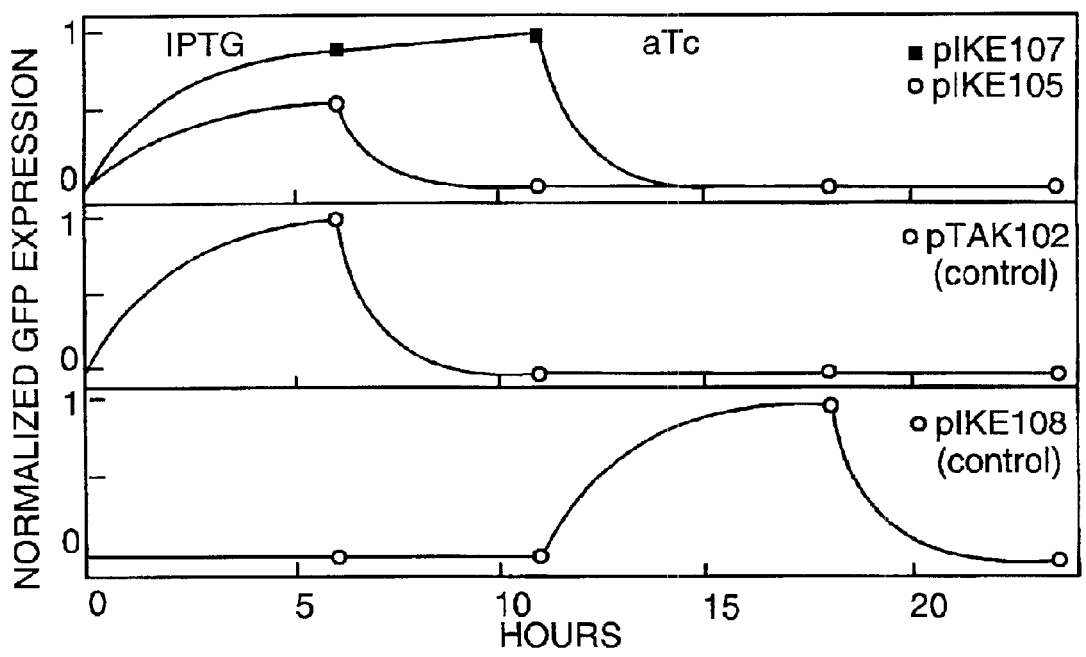

The existence of bistability is illustrated in FIG. 9. In this experiment, the toggle and control plasmids were grown in E. coli strain JM2.300 for 23.5 hours. At 6, 11, 18 and 23.5 hours, samples were taken and cells were pelleted, washed once in LB or PBS, and diluted 500–1000 fold into fresh medium with or without inducers as appropriate. Cells were initially grown for 6 hours with 2 mM IPTG, inducing GFPmut3 expression in all toggles and the IPTG-inducible pTAK102 control plasmid (FIGS. 9A and 9B). The thermally-inducible pTAK106 control (FIG. 9A) and the aTc-inducible pIKE108 control (FIG. 9B) did not express GFPmut3 in the presence of IPTG. Cells were washed and diluted into fresh medium with no IPTG and grown an additional 5 hours. The five bistable toggle plasmids, which had been switched to the high state by the IPTG pulse, continued to express GFPmut3 in the absence of inducer, while the pTAK102 control plasmid and the monostable pIKE105 toggle plasmid, returned to the low state (FIGS. 9A and 9B). Cells were diluted into fresh medium and induced at 42° C. (pTAK plasmids only—FIG. 9A) or grown in the presence of 500 ng/ml aTc (PIKE plasmids only—FIG. 12B). After 7 hours growth, GFPmut3 expression in all toggles had been shut off, while GFPmut3 expression in the thermally-inducible pTAK106 control and the aTc-inducible pIKE108 control was up-regulated. Cells were washed and diluted into fresh medium with no inducers or returned to standard temperature. After an additional 5.5 hours, the five bistable toggle plasmids, which had been switched to the low state, continued to repress GFPmut3 expression, while the pTAK106 and pIKE108 controls returned, as expected, to their non-induced condition.

Figure 9C:
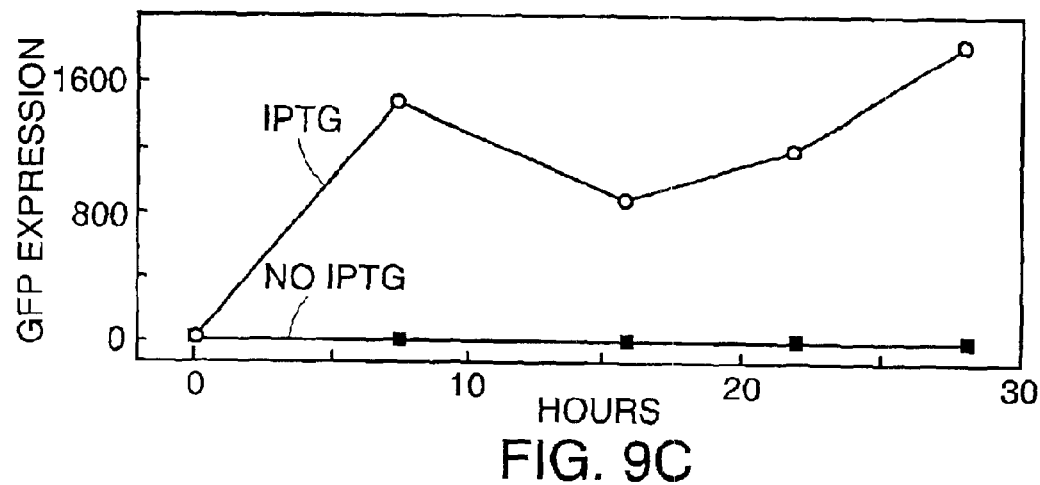

FIG. 9C shows the long-term stability of the two states of the pTAK117 toggle switch. In this experiment, a single culture of pTAK117 cells (initially in the low state) was divided into two groups and diluted. The first group was grown in medium with no inducers (squares) while the second group was grown in medium plus 2 mM IPTG (circles). After 6 hours, cells were pelleted, washed once in LB and diluted 1000 fold into fresh medium with no inducer. Both groups of cells were grown for an additional 22 hours while taking samples and diluting into fresh medium every 6–8.5 hours. The two groups of pTAK117 cells remained in their initial high or low states for the entire 22 hour period.

Although all of the toggle plasmids contained the same configuration of elements, one plasmid, pIKE105, did not exhibit bistability. This result probably is due to the reduced efficiency of the TetR repressor relative to the λ repressor. To maintain bistability, the reduced efficiency requires a corresponding decrease in the strength of the $P_L$tetO-1 promoter relative to the $P_L$Slcon promoter. The $P_L$tetO-1 in the pIKE105 plasmid apparently is not sufficiently reduced in strength to achieve bistability. However, the strength reduction provided by the $P_L$tetO-1 promoter in the pIKE107 plasmid is sufficient.

Example 4

Figure 10A:
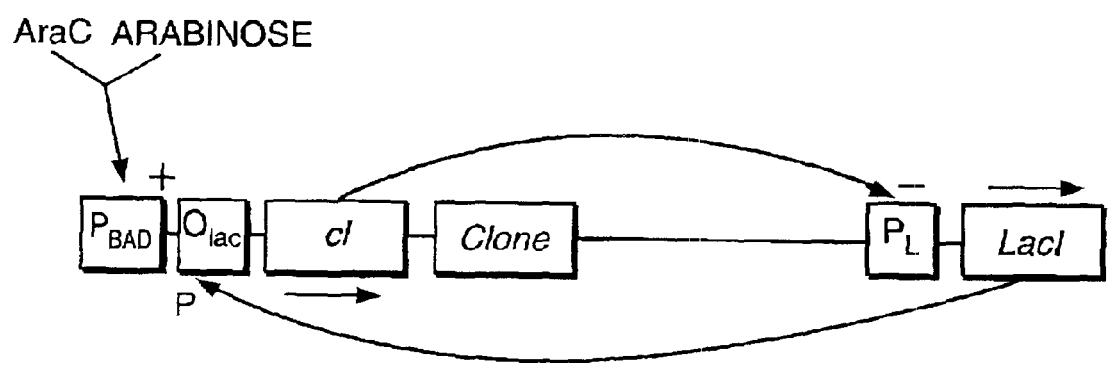
FIG. 10 provides illustrations of an exemplary eukaryotic adjustable-threshold toggle switch (FIG. 10A) and nucleic acid sequences of the $P_{bad}$ promoter fused to the $O_{lac}$ operator region of the $P_{trc}$ promoter (FIG. 10B).

Design and Construction of a Plasmid Carrying an Exemplary Adjustable-Threshold Switch The experimental methods used to construct and test adjustable-threshold switch constructs are similar to those discussed for the toggle switch constructs described in U.S. Ser. No. 09/872,868. It is contemplated that lements of an adjustable-threshold switch construct may be arranged in the same configuration as those in the toggle switch construct except that one of the constitutive promoters is replaced by a promoter from which transcription can be activated by an activating agent (see FIG. 10A). Additionally, expression from this promoter is preferably negligible in the absence of an activating agent. Finally, this promoter is preferably simultaneously suppressed by the opposing gene in the switch construct (i.e., regulatory gene 2 ($R_2$) in FIGS. 1A and 1B). Construction of a promoter that satisfies all of the above requirements is facilitated by the modular structure of the $P_{trc}$ promoter used in Example 1. The Lac repressor binding site begins at the first nucleotide of the mRNA transcript. The complete $P_{trc}$ promoter, including all of the RNAP recognition sites, is located upstream of the Lac repressor binding site. Thus, the entire $P_{trc}$ promoter upstream of the +1 nucleotide may be removed and replaced by nearly any positively regulated promoter element, such as the promoters set forth in Table 2. The new hybrid promoter, which retains the Lac repressor binding site, is thus both positively and negatively regulated. For example, the $P_{bad}$ promoter, which is activated by the AraC protein in the presence of arabinose, is fused to the $O_{lac}$ operator region of $P_{trc}$ (FIG. 10B, and SEQ ID NO: 12). The resulting hybrid promoter is positively activated by AraC-arabinose and repressed by lacI (FIG. 10A).

The opposing promoter may remain unaltered, or its strength may be modified in order to adjust the threshold location or hysteresis. Such strength modifications may also be necessary for the hybrid activator/repressor promoter.

The modifications can be introduced through standard recombinant DNA techniques.

Dynamic adjustment of the threshold concentration of the inducing agent exemplified by activating agent in FIG. 1A or 1B is also possible. Because the strengths of the promoters ($\alpha_1$ and $\alpha_2$) are dependent on the strength of repressor-DNA binding, an inducer compound such as IPTG can be used to alter the promoter strength. The inducer, by competitively binding the repressor, effectively raises the dissociation constant of the repressor-DNA binding. Thus, by adjusting the concentration of inducer in the medium, the threshold can be dynamically altered.

Many suitable activatable promoters are known in the art. These and their cognate activators are exemplified by the activators/promoters discussed herein.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

INCORPORATION BY REFERENCE

Each of the patent documents and scientific publications disclosed herein is incorporated by reference into this application in its entirety.

What is claimed is:

1. A recombinant adjustable threshold genetic switch comprising:
   (a) a first nucleic acid construct comprising an inducible promoter operably associated with a first gene encoding a first repressor protein; and
   (b) a second nucleic acid construct comprising a promote operably associated with a second gene encoding a second repressor protein, wherein transcription from the promoter is active in the absence of a repressor, and
   wherein the first repressor protein, when produced, is capable of repressing transcription from the promoter from which transcription is active in the absence of a repressor, and wherein transcription of the first gene encoding the first repressor protein is inducible by an activating agent, and
   wherein the second repressor protein, when produced, is capable of repressing transcription from the inducible promoter, and wherein the activating agent induces transcription from the inducible promoter by a mechanism other than inhibiting expression or activity of the second repressor and is required for activity of the inducible promoter.

2. The genetic switch of claim 1, wherein upon exposure to a threshold amount of the agent, the inducible promoter transcribes the first gene to produce the first repressor protein in an amount sufficient to repress transcription from the promoter from which transcription is active in the absence of a repressor.

3. The genetic switch of claim 2, whereby reduction in the amount of the activating agent results in decreased transcription of the first gene encoding the first repressor protein.

4. The genetic switch of claim 3, whereby reduction in the amount of the activating agent results in derepression of the promoter from which transcription is active in the absence of a repressor, thereby increasing transcription of the second gene encoding the second repressor protein.

5. The genetic switch of claim 1, wherein the inducible promoter, the promoter from which transcription is active in the absence of a repressor, or both promoters are in operable association with an operator.

6. The genetic switch of claim 1, wherein the first construct further comprises a third gene encoding a protein of interest, wherein the third gene is in operable association with the inducible promoter.

7. The genetic switch of claim 6, wherein transcription of the third gene is increased by the activating agent.

8. The genetic switch of claim 1 or 6, wherein the second construct further comprises a fourth gene encoding a protein of interest, wherein the fourth gene is in operable association with the promoter from which transcription is active in the absence of a repressor.

9. The genetic switch of claim 8, wherein transcription of the fourth gene is repressible by the activating agent.

10. The genetic switch of claim 1, wherein the first and second nucleic acid constructs are comprised within a single contiguous nucleic acid molecule.

11. An isolated host cell harboring the genetic switch of claim 1.

12. A host cell harboring the genetic switch of claim 1, wherein the host cell is a prokaryotic cell.

13. The host cell of claim 12, wherein the prokaryotic cell is *Escherichia coli*.

14. The host cell of claim 11, wherein the host cell is a eukaryotic cell.

15. The host cell of claim 14, wherein the eukaryotic cell is a mammalian cell or a yeast cell.

* * * * *

SEQUENCE LISTING

<160> NUMBER OF SEQ ID NOS: 12

<210> SEQ ID NO 1
<211> LENGTH: 90
<212> TYPE: DNA
<213> ORGANISM: Artificial Sequence
<220> FEATURE:
<223> OTHER INFORMATION: Promoter Ptrc-2

<400> SEQUENCE: 1
ccatcgaatg gctgaaatga gctgttgaca attaatcatc cggctcgtat aatgtgtgga      60
attgtgagcg gataacaatt tcacacagga      90

<210> SEQ ID NO 2
<211> LENGTH: 102
<212> TYPE: DNA
<213> ORGANISM: Artificial Sequence
<220> FEATURE:
<223> OTHER INFORMATION: Promoter PL-s1con

<400> SEQUENCE: 2
gcatgcacag ataaccatct gcggtgataa attatctctg gcggtgttga cataaatacc      60
actggcggtt ataatgagca catcagcagg gtatgcaaag ga      102

<210> SEQ ID NO 3
<211> LENGTH: 84
<212> TYPE: DNA
<213> ORGANISM: Artificial Sequence
<220> FEATURE:
<223> OTHER INFORMATION: Promoter Pltet0-1

<400> SEQUENCE: 3
gcatgctccc tatcagtgat agagattgac atccctatca gtgatagaga tactgagcac      60
atcagcagga cgcactgacc agga      84

<210> SEQ ID NO 4
<211> LENGTH: 15
<212> TYPE: DNA
<213> ORGANISM: Artificial Sequence
<220> FEATURE:
<223> OTHER INFORMATION: Ribosome Binding Site A

<400> SEQUENCE: 4
aggaggaaaa aaatg      15

```
<210> SEQ ID NO 5
<211> LENGTH: 13
<212> TYPE: DNA
<213> ORGANISM: Artificial Sequence
<220> FEATURE:
<223> OTHER INFORMATION: Ribosome Binding Site B

<400> SEQUENCE: 5
aggaatttaa atg                                                    13

<210> SEQ ID NO 6
<211> LENGTH: 15
<212> TYPE: DNA
<213> ORGANISM: Artificial Sequence
<220> FEATURE:
<223> OTHER INFORMATION: Ribosome Binding Site C

<400> SEQUENCE: 6
aggaaacaga ccatg                                                  15

<210> SEQ ID NO 7
<211> LENGTH: 17
<212> TYPE: DNA
<213> ORGANISM: Artificial Sequence
<220> FEATURE:
<223> OTHER INFORMATION: Ribosome Binding Site D

<400> SEQUENCE: 7
aggaaaccgg ttcgatg                                                17

<210> SEQ ID NO 8
<211> LENGTH: 15
<212> TYPE: DNA
<213> ORGANISM: Artificial Sequence
<220> FEATURE:
<223> OTHER INFORMATION: Ribosome Binding Site E

<400> SEQUENCE: 8
aggaaaccgg ttatg                                                  15

<210> SEQ ID NO 9
<211> LENGTH: 14
<212> TYPE: DNA
<213> ORGANISM: Artificial Sequence
<220> FEATURE:
<223> OTHER INFORMATION: Ribosome Binding Site F

<400> SEQUENCE: 9
aggacggttc gatg                                                   14

<210> SEQ ID NO 10
<211> LENGTH: 16
<212> TYPE: DNA
<213> ORGANISM: Artificial Sequence
<220> FEATURE:
<223> OTHER INFORMATION: Ribosome Binding Site G

<400> SEQUENCE: 10
aggaaaggcc tcgatg                                                 16

<210> SEQ ID NO 11
<211> LENGTH: 14
<212> TYPE: DNA
<213> ORGANISM: Artificial Sequence
<220> FEATURE:
<223> OTHER INFORMATION: Ribosome Binding Site H
```

```
<400> SEQUENCE: 11
aggacggccg gatg                                                          14

<210> SEQ ID NO 12
<211> LENGTH: 146
<212> TYPE: DNA
<213> ORGANISM: Artificial Sequence
<220> FEATURE:
<223> OTHER INFORMATION: Pbad promoter fused to the Olac operator region
      of the Ptrc promote

<400> SEQUENCE: 12
gcgtcacact ttgctatgcc atagcatttt tatccataag attagcggat cctacctgac          60
gctttttatc gcaactctct actgtttctc catagatcta atgtgtggaa ttgtgagcgg         120
ataacaattt cacacaggaa accggt                                             146
```